United States Patent
Sogoh et al.

(10) Patent No.: US 10,124,326 B2
(45) Date of Patent: Nov. 13, 2018

(54) MODIFIED SOLID POLYALKYLALUMINOXANE AND CATALYST FOR OLEFIN OLIGOMERIZATION REACTION

(71) Applicant: Sumitomo Chemical Company, Limited, Chuo-ku, Tokyo (JP)

(72) Inventors: Kenji Sogoh, Ichihara (JP); Yohei Kashiwame, Ichihara (JP); Takahiro Hino, Chiba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 37 days.

(21) Appl. No.: 15/515,390

(22) PCT Filed: Sep. 24, 2015

(86) PCT No.: PCT/JP2015/076975
§ 371 (c)(1),
(2) Date: Mar. 29, 2017

(87) PCT Pub. No.: WO2016/052308
PCT Pub. Date: Apr. 7, 2016

(65) Prior Publication Data
US 2017/0225155 A1   Aug. 10, 2017

(30) Foreign Application Priority Data

Sep. 30, 2014 (JP) .................. 2014-199907
Apr. 16, 2015 (JP) .................. 2015-083980

(51) Int. Cl.
| | |
|---|---|
| C08F 4/02 | (2006.01) |
| C07C 2/32 | (2006.01) |
| C07C 2/30 | (2006.01) |
| B01J 31/22 | (2006.01) |
| B01J 31/14 | (2006.01) |
| C08G 79/10 | (2006.01) |
| B01J 31/16 | (2006.01) |
| C07F 5/06 | (2006.01) |
| C07F 7/08 | (2006.01) |
| C08G 79/12 | (2006.01) |

(52) U.S. Cl.
CPC ......... *B01J 31/143* (2013.01); *B01J 31/1616* (2013.01); *B01J 31/22* (2013.01); *B01J 31/2226* (2013.01); *B01J 31/2295* (2013.01); *C07C 2/30* (2013.01); *C07C 2/32* (2013.01); *C07F 5/068* (2013.01); *C07F 7/08* (2013.01); *C08F 4/02* (2013.01); *C08G 79/10* (2013.01); *C08G 79/12* (2013.01); *B01J 2231/20* (2013.01); *B01J 2531/40* (2013.01); *B01J 2531/46* (2013.01)

(58) Field of Classification Search
CPC ........ C08F 4/02; C08F 4/65912; C08F 4/642; C07F 2/30; C07F 2/32; C01J 31/143; C01J 31/2295
See application file for complete search history.

(56) References Cited

U.S. PATENT DOCUMENTS

| | | | |
|---|---|---|---|
| 4,952,540 A * | 8/1990 | Kioka | ...... C07F 5/068 502/103 |
| 5,856,257 A | 1/1999 | Freeman et al. | |
| 6,100,213 A | 8/2000 | Kumamoto et al. | |
| 6,153,550 A | 11/2000 | Kissin | |

(Continued)

FOREIGN PATENT DOCUMENTS

| | | |
|---|---|---|
| EP | 2955187 A1 | 12/2015 |
| JP | H06329714 A | 11/1994 |

(Continued)

OTHER PUBLICATIONS

Extended Search Report dated Apr. 26, 2018 in EP Application No. 15845988.3.
Int'l Search Report dated Oct. 27, 2015 in Int'l Application No. PCT/JP2015/076975.
Int'l Preliminary Report on Patentability dated Apr. 4, 2017 in Int'l Application No. PCT/JP2015/076975.
Office Action dated Jun. 4, 2018 in GC Application No. 2015/30114.

*Primary Examiner* — Caixia Lu
(74) *Attorney, Agent, or Firm* — Panitch Schwarze Belisario & Nadel LLP

(57) ABSTRACT

A modified solid polyalkylaluminoxane is provided, which is capable of providing α-olefin suppressing adhesion of any polymer produced as a by-product onto the reactor wall and the stirrer, and which is capable of providing a highly active olefin oligomerization reaction catalyst. An olefin oligomerization reaction catalyst containing the modified solid polyalkylaluminoxane is also provided. The modified solid polyalkylaluminoxane for olefin oligomerization reactions contains structural units represented by general formula (a) and structural units represented by general formula (b), whose median diameter is equal to or larger than 0.1 μm and equal to or smaller than 50 μm,

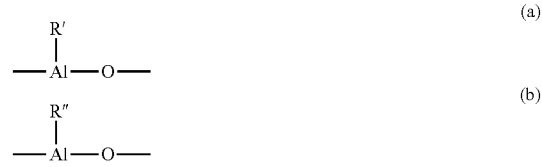

in which R' in the general formula (a) represents an alkyl group having 1 to 20 carbon atoms, and R" in the general formula (b) represents a halogenated alkoxy group having 1 to 20 carbon atoms or a halogenated aryloxy group having 6 to 20 carbon atoms.

6 Claims, No Drawings

(56) References Cited

U.S. PATENT DOCUMENTS

| | | | |
|---|---|---|---|
| 6,197,985 B1 * | 3/2001 | Kobata | C07F 5/068 502/103 |
| 6,548,443 B1 | 4/2003 | Watanabe | |
| 2007/0197745 A1 | 8/2007 | Koji et al. | |
| 2011/0082325 A1 | 4/2011 | Suzuki et al. | |
| 2011/0282017 A1 * | 11/2011 | Kaji | C07F 5/066 526/160 |
| 2012/0184431 A1 | 7/2012 | Kawashima et al. | |
| 2012/0184693 A1 | 7/2012 | Kawashima et al. | |
| 2013/0005931 A1 | 1/2013 | Kawashima et al. | |
| 2013/0059990 A1 | 3/2013 | Koji et al. | |
| 2015/0057418 A1 * | 2/2015 | Kaji | C08F 4/65912 526/160 |

FOREIGN PATENT DOCUMENTS

| | | |
|---|---|---|
| JP | H09249707 A | 9/1997 |
| JP | H11140113 A | 5/1999 |
| JP | 2000038410 A | 2/2000 |
| JP | 2000095810 A | 4/2000 |
| JP | 2001139617 A | 5/2001 |
| JP | 2002508402 A | 3/2002 |
| JP | 2002293785 A | 10/2002 |
| JP | 2005263749 A | 9/2005 |
| JP | 2005306989 A | 11/2005 |
| JP | 200972665 A | 4/2009 |
| JP | 201198954 A | 5/2011 |
| JP | 2011178682 A | 9/2011 |
| JP | 2012213765 A | 11/2012 |
| JP | 2012224842 A | 11/2012 |
| JP | 2013049783 A | 3/2013 |
| JP | 2013060400 A | 4/2013 |
| JP | 2013095671 A | 5/2013 |
| WO | 2009005003 A1 | 1/2009 |
| WO | 2010055652 A1 | 5/2010 |
| WO | 2011142400 A1 | 11/2011 |
| WO | 2012133921 A1 | 10/2012 |
| WO | 2012133936 A1 | 10/2012 |
| WO | 2013146337 A1 | 10/2013 |
| WO | 2014123212 A1 | 8/2014 |

* cited by examiner

MODIFIED SOLID POLYALKYLALUMINOXANE AND CATALYST FOR OLEFIN OLIGOMERIZATION REACTION

CROSS-REFERENCE TO RELATED APPLICATION

This application is a Section 371 of International Application No. PCT/JP2015/076975, filed Sep. 24, 2015, which was published in the Japanese language on Apr. 7, 2016 under International Publication No. WO 2016/052308 A1, and the disclosure of which is incorporated herein by reference.

TECHNICAL FIELD

The present application claims the priority of the Paris Convention based on Japanese Patent Application Nos. 2014-199907 (filed on Sep. 30, 2014) and 2015-083980 (filed on Apr. 16, 2015), and the entire contents of the aforementioned applications are incorporated herein by reference.

The present invention relates to a modified solid polyalkylaluminoxane and an olefin oligomerization reaction catalyst, and specifically to a modified solid polyalkylaluminoxane capable of producing an α-olefin suppressing adhesion of any polymer produced as a by-product onto the reactor wall and the stirrer and capable of providing a highly active olefin oligomerization reaction catalyst, and an olefin oligomerization reaction catalyst comprising the modified solid polyalkylaluminoxane.

BACKGROUND ART

α-Olefins are compounds industrially used widely as raw materials of polyolefins. Olefin oligomerization reactions are reactions capable of producing α-olefins, and catalysts capable of producing α-olefins with high selectivity have recently been developed for the olefin oligomerization reaction (Patent Documents 1 to 5).

PRIOR ART DOCUMENTS

Patent Documents

Patent Document 1: U.S. Pat. No. 5,856,257
Patent Document 2: Japanese Laid-Open Patent Publication No. 2011-98954
Patent Document 3: Japanese Laid-Open Patent Publication No. 2012-213765
Patent Document 4: WO 2009-005003
Patent Document 5: Japanese Laid-Open Patent Publication No. 2011-178682

SUMMARY OF THE INVENTION

Problems to be Solved by the Invention

The activity of the catalysts described in each of Patent Documents is however not necessarily satisfactory. When α-olefins are produced in an olefin oligomerization reaction using the catalyst described in each of Patent Documents, a long-term operation is difficult because a polymer produced as a by-product adheres onto the reactor wall and the stirrer.

Under this circumstance, the problems to be solved by the present invention is to provide a modified solid polyalkylaluminoxane capable of producing α-olefins suppressing adhesion of any polymer produced as a by-product onto the reactor wall and the stirrer and capable of providing a highly active olefin oligomerization reaction catalyst, and to provide an olefin oligomerization reaction catalyst comprising the modified solid polyalkylaluminoxane.

Means for Solving Problems

The present invention relates to a modified solid polyalkylaluminoxane for olefin oligomerization reactions, the modified polyalkylaluminoxane having a median diameter of 0.1 μm to 50 μm and comprising structural units represented by the following general formula (a) and structural units represented by the following general formula (b),

in which

R' in the general formula (a) represents an alkyl group having 1 to 20 carbon atoms, and R" in the general formula (b) represents a halogenated alkoxy group having 1 to 20 carbon atoms or a halogenated aryloxy group having 6 to 20 carbon atoms.

Effect of the Invention

According to the present invention, such substances can be provided as a modified solid polyalkylaluminoxane capable of producing α-olefins suppressing adhesion of any polymer produced as a by-product onto the reactor wall and the stirrer and capable of providing highly active olefin oligomerization reaction catalysts, and olefin oligomerization reaction catalysts comprising the modified solid polyalkylaluminoxane.

MODES FOR CARRYING OUT THE INVENTION

The modified solid polyalkylaluminoxane of the present invention is a modified solid polyalkylaluminoxane for olefin oligomerization reactions, the modified polyalkylaluminoxane having a median diameter of 0.1 μm to 50 μm and comprising structural units represented by the following general formula (a) and structural units represented by the following general formula (b). The modified solid polyalkylaluminoxane may be either one comprising the structural units each represented by the following general formula (a) and the structural units each represented by the other following general formula (b) linked together in a chain or one comprising these structural units linked together in a ring, or alternatively may be a mixture thereof. The modified solid polyalkylaluminoxane may comprise the structural units each represented by the following general formula (a) and the structural units each represented by the other following general formula (b) that are bonded to each other in random order.

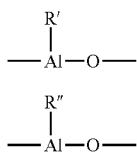

R' in the general formula (a) represents an alkyl group having 1 to 20 carbon atoms. The alkyl group having 1 to 20 carbon atoms as R' can be a methyl group, an ethyl group, an n-propyl group, a cyclopropyl group, an isopropyl group, an n-butyl group, an isobutyl group, a sec-butyl group, a tert-butyl group, a cyclobutyl group, an n-pentyl group, an isopentyl group, a neopentyl group, a 1-methylbutyl group, a 2-methylbutyl group, a 1-ethylpropyl group, a 1,1-dimethylpropyl group, a 1,2-dimethylpropyl group, a cyclopentyl group, an n-hexyl group, a cyclohexyl group, an n-heptyl group, an n-octyl group, an n-nonyl group, an n-decyl group, an n-undecyl group, an n-dodecyl group, an n-tetradecyl group, an n-hexadecyl group, an n-octadecyl group, and an n-icosyl group. Preferably, a methyl group, an ethyl group, an isobutyl group, a hexyl group, or an octyl group is employed. More preferably, a methyl group, an ethyl group, or an isobutyl group is employed. Yet more preferably, a methyl group or an isobutyl group is employed.

R" in the general formula (b) represents a halogenated alkoxy group having 1 to 20 carbon atoms or a halogenated aryloxy group having 6 to 20 carbon atoms.

The halogenated alkoxy group having 1 to 20 carbon atoms as R" can be a fluoromethoxy group, a chloromethoxy group, a bromomethoxy group, an iodomethoxy group, a difluoromethoxy group, a dichloromethoxy group, a dibromomethoxy group, a diiodomethoxy group, a trifluoromethoxy group, a trichloromethoxy group, a tribromomethoxy group, a triiodomethoxy group, a 2,2,2-trifluoroethoxy group, a 2,2,2-trichloroethoxy group, a 2,2,2-tribromoethoxy group, a 2,2,2-triiodoethoxy group, a 2,2,3,3,3-pentafluoropropoxy group, a 2,2,3,3,3-pentachloropropoxy group, a 2,2,3,3,3-pentabromopropoxy group, a 2,2,3,3,3-pentaiodopropoxy group, a 2,2,2-trifluoro-1-(trifluoromethyl)ethoxy group, a 2,2,2-trichloro-1-(trichloromethyl)ethoxy group, a 2,2,2-tribromo-1-(tribromomethyl)ethoxy group, a 2,2,2-triiodo-1-(triiodomethyl) ethoxy group, a 1,1-bis(trifluoromethyl)-2,2,2-trifluoroethoxy group, a 1,1-bis(tribromomethyl)-2,2,2-tribromoethoxy group, a 1,1-bis(triiodomethyl)-2,2,2-triiodoethoxy group, and a perfluoro-n-buthoxy group.

The halogenated aryloxy group having 6 to 20 carbon atoms as R" can be a 2-fluorophenoxy group, a 3-fluorophenoxy group, a 4-fluorophenoxy group, a 2,4-difluorophenoxy group, a 2,6-difluorophenoxy group, 3,4-difluorophenoxy group, a 3,5-difluorophenoxy group, a 2,4,6-trifluorophenoxy group, a 3,4,5-trifluorophenoxy group, a 2,3,5,6-tetrafluorophenoxy group, a pentafluorophenoxy group, a 2,3,5,6-tetrafluoro-4-(trifluoromethyl)phenoxy group, a 2,3,5,6-tetrafluoro-4-(pentafluorophenyl)phenoxy group, a perfluoro-1-naphthoxy group, a perfluoro-2-naphthoxy group, a 2-chlorophenoxy group, a 3-chlorophenoxy group, a 4-chlorophenoxy group, a 2,4-dichlorophenoxy group, a 2,6-dichlorophenoxy group, a 3,4-dichlorophenoxy group, a 3,5-dichlorophenoxy group, a 2,4,6-trichlorophenoxy group, a 3,4,5-trichlorophenoxy group, a 2,3,5,6-tetrachlorophenoxy group, a pentachlorophenoxy group, a 2,3,5,6-tetrachloro-4-(trichloromethyl)phenoxy group, a 2,3,5,6-tetrachloro-4-(pentachlorophenyl)phenoxy group, a perchloro-1-naphthoxy group, a perchloro-2-naphthoxy group, a 2-bromophenoxy group, a 3-bromophenoxy group, a 4-bromophenoxy group, a 2,4-dibromophenoxy group, a 2,6-dibromophenoxy group, a 3,4-dibromophenoxy group, a 3,5-dibromophenoxy group, a 2,4,6-tribromophenoxy group, a 3,4,5-tribromophenoxy group, a 2,3,5,6-tetrabromophenoxy group, a pentabromophenoxy group, a 2,3,5,6-tetrabromo-4-(tribromomethyl)phenoxy group, a 2,3,5,6-tetrabromo-4-(pentabromophenyl)phenoxy group, a perbromo-1-naphthoxy group, a perbromo-2-naphthoxy group, a 2-iodophenoxy group, a 3-iodophenoxy group, a 4-iodophenoxy group, a 2,4-diiodophenoxy group, a 2,6-diiodophenoxy group, a 3,4-diiodophenoxy group, a 3,5-diiodophenoxy group, a 2,4,6-triiodophenoxy group, a 3,4,5-triiodophenoxy group, a 2,3,5,6-tetraiodophenoxy group, a pentaiodophenoxy group, a 2,3,5,6-tetraiodo-4-(triiodomethyl)phenoxy group, a 2,3,5,6-tetraiodo-4-(pentaiodophenyl)phenoxy group, a periodo-1-naphthoxy group, a periodo-2-naphthoxy group, a 2-(trifluoromethyl)phenoxy group, a 3-(trifluoromethyl)phenoxy group, a 4-(trifluoromethyl)phenoxy group, a 2,6-bis(trifluoromethyl)phenoxy group, a 3,5-bis(trifluoromethyl)phenoxy group, a 2,4,6-tris(trifluoromethyl)phenoxy group, and a 3,4,5-tris(trifluoromethyl)phenoxy group.

Preferably, a halogenated aryloxy group is employed as R". More preferably, a fluoroaryloxy group is employed as R". Yet more preferably, a substance is employed as R", such as a 2,4,6-trifluorophenoxy group, a 3,4,5-trifluorophenoxy group, a pentafluorophenoxy group, a 2,6-bis(trifluoromethyl)phenoxy group, a 3,5-(bistrifluoromethyl)phenoxy group, or a 2,4,6-tris(trifluoromethyl)phenoxy group. Yet much more preferably, a pentafluorophenoxy group is employed as R".

Preferably, the ratio ($m/(m+n)$) of the number (m) of the structural units represented by the general formula (b) to the total of the number (n) of the structural units represented by the general formula (a) and the number (m) of the structural units represented by the general formula (b) of the modified solid polyalkylaluminoxane is 0.05 to 0.5.

The ratio ($m/(m+n)$) is calculated from the ratios of the aluminum atoms, the fluorine atoms, the carbon atoms, the oxygen atoms, and the hydrogen atoms constituting the modified solid polyalkylaluminoxane determined by elementally analyzing the modified solid polyalkylaluminoxane.

The method of the elemental analysis can be a known method such as ICP spectrometry or EPMA analysis.

The modified solid polyalkylaluminoxane is in a particle form and has a median diameter, preferably, of 0.1 µm to 50 µm and, more preferably, 1 µm to 30 µm. Preferably, the particle size distribution is narrow. The median diameter and the particle size distribution of the modified solid polyalkylaluminoxane can be determined using a laser diffraction scattering method in a dried hydrocarbon solvent using a laser diffraction particle size distribution measuring apparatus.

The particle size distribution can be represented by a Span value and a smaller Span value indicates a narrower particle size distribution. Preferably, the Span value is equal to or smaller than 2. The Span value can be determined according to the following equation using the values of D10 representing the particle diameter whose cumulative distribution determined by the laser diffraction particle size distribution measurement is 10%, D50 for 50% (the median diameter), and D90 for 90%.

$$\text{Span value}=(D90-D10)/D50$$

Preferably, at an equilibrium state at 25° C. in n-hexane or toluene, the ratio of the molar number of aluminum atoms dissolved in the solvent to the molar number of aluminum atoms in the modified solid polyalkylaluminoxane of the present invention is 0 mol % to 2 mol %.

The modified solid polyalkylaluminoxane is acquired by reacting a solid polyalkylaluminoxane with a halogenated alcohol including 1 to 20 carbon atoms or a halogenated phenol including 6 to 20 carbon atoms. The "phenol" in "halogenated phenol" is a generic name of compounds each including a hydroxy group on an aromatic ring.

Preferably, the content of aluminum atoms contained in the solid polyalkylaluminoxane is 36 wt % to 43 wt %. For this, the overall amount of the solid polyalkylaluminoxane is 100 wt %. The content of aluminum atoms contained in the solid polyalkylaluminoxane can be determined using a known approach such as, for example, an approach described in WO 2010-055652.

Preferably, the solid polyalkylaluminoxane is used whose median diameter is equal to or smaller than 50 μm and whose particle size distribution is narrower. The median diameter and the particle size distribution thereof can be determined by the laser diffraction particle size distribution measuring apparatus similarly to the modified solid polyalkylaluminoxane. Preferably, the Span value to be the index of the particle size distribution is equal to or smaller than 2.

The solid polyalkylaluminoxane can be a solid polymethylaluminoxane, a solid polymethylisobutylaluminoxane, and a solid polyisobutylaluminoxane, and is, preferably, a solid polymethylaluminoxane.

The production method of the solid polyalkylaluminoxane can be a method according to which an aromatic hydrocarbon solution including polyalkylaluminoxane and trialkyl aluminum is heated at a reduced pressure to remove the aromatic hydrocarbon solvent and trialkyl aluminum and the residue is dried to acquire the solid polyalkylaluminoxane, a method according to which an aromatic hydrocarbon solution including polyalkylaluminoxane and trialkyl aluminum is added to an aliphatic hydrocarbon solvent and the solid polyalkylaluminoxane is thereby precipitated to be acquired, and a method according to which an aromatic hydrocarbon mixture solution including polyalkylaluminoxane and trialkyl aluminum is heated to cause the solid polyalkylaluminoxane to be precipitated to be acquired. More preferably, the method of heating an aromatic hydrocarbon solution including polyalkylaluminoxane and trialkyl aluminum is used. Preferably, the heating temperature is 80° C. to 200° C. Preferably, the heating time period is 5 minutes to 24 hours.

The production method of polyalkylaluminoxane can be a method of reacting alkyl aluminum and water with each other, and a method of pyrolyzing an alkyl aluminum compound including an aluminum-oxygen-carbon bond acquired by reacting an oxygen-including organic compound and trialkyl aluminum with each other. Preferably, the method is used of pyrolyzing a compound acquired by reacting an oxygen-including organic compound and trialkyl aluminum with each other. Preferably, carboxylic acid is used as the oxygen-including organic compound.

The halogen in the halogenated alcohol including 1 to 20 carbon atoms or the halogenated phenol including 1 to 20 carbon atoms can be fluorine, chlorine, bromine, or iodine.

The halogenated alcohol including 1 to 20 carbon atoms can be fluoromethanol, difluoromethanol, trifluoromethanol, chloromethanol, dichloromethanol, trichloromethanol, bromomethanol, dibromomethanol, tribromomethanol, iodomethanol, diiodomethanol, triiodomethanol, fluoroethanol, difluoroethanol, trifluoroethanol, tetrafluoroethanol, pentafluoroethanol, chloroethanol, dichloroethanol, trichloroethanol, tetrachloroethanol, pentachloroethanol, bromoethanol, dibromoethanol, tribromoethanol, tetrabromoethanol, pentabromoethanol, perfluoro-1-propanol, perfluoro-2-propanol, perfluoro-1-butanol, perfluoro-2-methyl-1-propanol, perfluoro-2-butanol, perfluoro-2-methyl-2-propanol, perfluoro-1-pentanol, perfluoro-1-hexanol, perfluoro-1-octanol, perfluoro-1-dodecanol, perfluoro-1-pentadecanol, perfluoro-1-icosanol, perchloro-1-propanol, perchloro-2-propanol, perchloro-1-butanol, perchloro-2-methyl-1-propanol, perchloro-2-butanol, perchloro-2-methyl-2-propanol, perchloro-1-pentanol, perchloro-1-hexanol, perchloro-1-octanol, perchloro-1-dodecanol, perchloro-1-pentadecanol, perchloro-1-icosanol, perbromo-1-propanol, perbromo-2-propanol, perbromo-1-butanol, perbromo-2-methyl-1-propanol, perbromo-2-butanol, perbromo-2-methyl-2-propanol, perbromo-1-pentanol, perbromo-1-hexanol, perbromo-1-octanol, perbromo-1-dodecanol, perbromo-1-pentadecanol, and perbromo-1-icosanol. The halogenated alcohol including 1 to 20 carbon atoms is, preferably, floroalcohol and, more preferably, trifluoromethanol, perfluoro-2-propanol, or perfluoro-2-methyl-2-propanol.

The halogenated phenol including 6 to 20 carbon atoms can be 2-fluorophenol, 3-fluorophenol, 4-fluorophenol, 2,4-difluorophenol, 2,6-difluorophenol, 3,4-difluorophenol, 3,5-difluorophenol, 2,4,6-trifluorophenol, 3,4,5-trifluorophenol, 2,3,5,6-tetrafluorophenol, pentafluorophenol, 2,3,5,6-tetrafluoro-4-(trifluoromethyl)phenol, 2,3,5,6-tetrafluoro-4-(pentafluorophenyl)phenol, 2,6-bis(trifluoromethyl)phenol, 3,5-bis(trifluoromethyl)phenol, 2,4,6-tris(trifluoromethyl)phenol, perfluoro-1-naphthol, perfluoro-2-naphthol, 2-chlorophenol, 3-chlorophenol, 4-chlorophenol, 2,4-dichlorophenol, 2,6-dichlorophenol, 3,4-dichlorophenol, 3,5-dichlorophenol, 2,4,6-trichlorophenol, 3,4,5-trichlorophenol, 2,3,5,6-tetrachlorophenol, pentachlorophenol, 2,3,5,6-tetrachloro-4-(trichloromethyl)phenol, 2,3,5,6-tetrachloro-4-(pentachlorophenyl)phenol, 2,6-bis(trichloromethyl)phenol, 3,5-bis(trichloromethyl)phenol, 2,4,6-tris(trichloromethyl)phynol, perchloro-1-naphthol, perchloro-2-naphthol, 2-bromophenol, 3-bromophenol, 4-bromophenol, 2,4-dibromophenol, 2,6-dibromophenol, 3,4-dibromophenol, 3,5-dibromophenol, 2,4,6-tribromophenol, 3,4,5-tribromophenol, 2,3,5,6-tetrabromophenol, pentabromophenol, 2,3,5,6-tetrabromo-4-(tribromomethyl)phenol, 2,3,5,6-tetrabromo-4-(pentabromophenyl)phenol, 2,6-bis(tribromomethyl)phenol, 3,5-bis(tribromomethyl)phenol, 2,4,6-tris(tribromomethyl)phenol, perbromo-1-naphthol, perbromo-2-naphthol, 2-iodophenol, 3-iodophenol, 4-iodophenol, 2,4-diiodophenol, 2,6-diiodophenol, 3,4-diiodophenol, 3,5-diiodophenol, 2,4,6-triiodophenol, 3,4,5-triiodophenol, 2,3,5,6-tetraiodophenol, pentaiodophenol, 2,3,5,6-tetraiodo-4-(triiodomethyl)phenol, 2,3,5,6-tetraiodo-4-(pentaiodophenyl)phenol, 2,6-bis(triiodomethyl)phenol, 3,5-bis(triiodomethyl)phenol, 2,4,6-tris(triiodomethyl)phenol, periodo-1-naphthol, and periodo-2-naphthol. The halogenated phenol including 6 to 20 carbon atoms is, preferably, a fluorophenol, is, more preferably, 2,4,6-trifluorophenol, 3,4,5-trifluorophenol, pentafluorophenol, 2,6-bis(trifluoromethyl)phenol, 3,5-bis(trifluoromethyl)phenol, or 2,4,6-tris(trifluoromethyl)phenol, and is, yet more preferably, pentafluorophenol.

The use amount of the halogenated alcohol having 1 to 20 carbon atoms or the halogenated phenol having 6 to 20 carbon atoms is preferably not less than 0.01 equivalents but less than 1.0 equivalent, more preferably not less than 0.05 equivalents but less than 1.0 equivalent, even more preferably 0.1 equivalents to 0.7 equivalents, and yet much more preferably 0.2 equivalents to 0.5 equivalents, to aluminum atoms in the modified solid polyalkylaluminoxane from the perspective that the activity of the olefin oligomerization reaction catalyst is maintained and the generation of any polymer as a by-product is suppressed.

Preferably, the solid polyalkylaluminoxane, and the halogenated alcohol having 1 to 20 carbon atoms or the halogenated phenol having 6 to 20 carbon atoms are reacted with each other in the presence of a solvent.

The method of reacting these substances in the presence of a solvent can be, for example, a method according to which the solid polyalkylaluminoxane is suspended in a solvent and the halogenated alcohol including having 1 to 20 carbon atoms or the halogenated phenol including having 6 to 20 carbon atoms is added thereto.

The solvent may be any solvent that is inert to the solid polyalkylaluminoxane. For example, the solvent can be an aromatic hydrocarbon solvent such as benzene or toluene and an aliphatic hydrocarbon solvent such as hexane or heptane. Each of these solvents may be used alone or two or more thereof may be used as a mixture. The use amount thereof is, preferably, 1 to 200 parts by weight and is, more preferably, 3 to 50 parts by weight, to one part by weight of the solid polyalkylaluminoxane.

The modified solid polyalkylaluminoxane may be used as slurry thereof that is acquired by the reaction in the presence of the solvent, or may be used as a solid substance thereof that is acquired by removing the supernatant liquid from the slurry by filtering etc., washing the residue using a solvent, and drying the residue.

The temperature for reacting the solid polyalkylaluminoxane and the halogenated alcohol or the halogenated phenol with each other is, preferably, equal to or higher than −100° C. and equal to or lower than the boiling point of the solvent and is, more preferably, −80° C. to 100° C.

The modified solid polyalkylaluminoxane is usable for the olefin oligomerization reaction. The olefin oligomerization reaction is a reaction to obtain, from an olefin, another olefin whose number of carbon atoms is a multiple number of the number of carbon atoms of the starting olefin. For example, the reaction is a reaction to produce 1-butene, 1-hexene, 1-octene, etc., from ethylene, or a reaction to produce 4-methyl-1-pentene, etc., from propylene. The olefin oligomerization reaction utilizing the modified solid polyalkylaluminoxane is, preferably, a reaction to produce α-olefins from ethylene and is, more preferably, a reaction to produce 1-hexene or 1-octene from ethylene.

The olefin oligomerization reaction catalyst comprises the modified solid polyalkylaluminoxane and a transition metal complex.

The transition metal complex can be a transition metal complex represented by the following general formula (2-1), a transition metal complex represented by the following general formula (2-2), a transition metal complex represented by the following general formula (2-3), a transition metal complex represented by the following general formula (2-4), or a transition metal complex represented by the following general formula (2-5).

Detailed description will be made for the transition metal complex represented by the following general formula (2-1), the transition metal complex represented by the following general formula (2-2), and the transition metal complex represented by the following general formula (2-3).

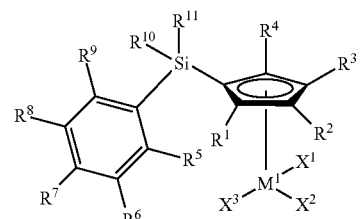

(2-1)

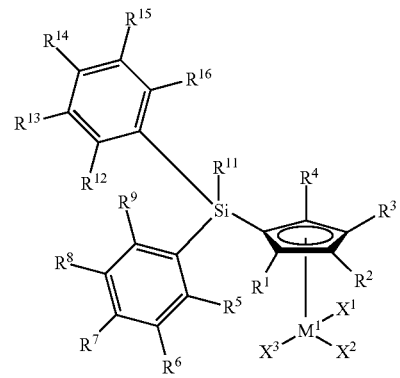

(2-2)

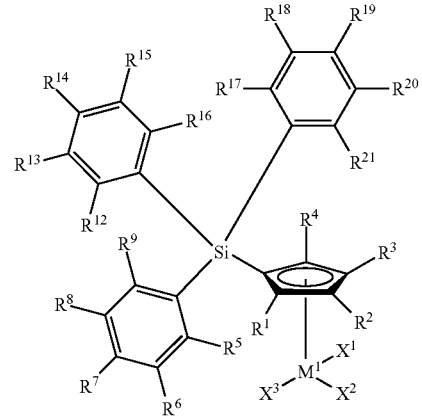

(2-3)

[$M^1$ in the general formula (2-1), the general formula (2-2), and the general formula (2-3) represents a transition metal atom of Group 4 of the periodic table of the elements.

$X^1$, $X^2$, $X^3$, $R^1$, $R^2$, $R^3$, $R^4$, $R^5$, $R^6$, $R^7$, $R^8$, and $R^9$ in the general formula (2-1), the general formula (2-2), and the general formula (2-3), $R^{12}$, $R^{13}$, $R^{14}$, $R^{15}$, and $R^{16}$ in the general formula (2-2) and the general formula (2-3), and $R^{17}$, $R^{18}$, $R^{19}$, $R^{20}$, and $R^{21}$ in the general formula (2-3) each independently represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group.

When two selected from $R^1$, $R^2$, $R^3$, and $R^4$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^1$, $R^2$, $R^3$, and $R^4$ may be bonded to each other at a site thereof formed by removing a hydrogen atom from the substituent group.

When two selected from $R^5$, $R^6$, $R^7$, $R^8$, and $R^9$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^5$, $R^6$, $R^7$, $R^8$, and $R^9$ may be bonded to each other at a site thereof formed by removing a hydrogen atom from the substituent group.

When two selected from $R^{12}$, $R^{13}$, $R^{14}$, $R^{15}$, and $R^{16}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{12}$, $R^{13}$, $R^{14}$, $R^{15}$, and $R^{16}$ may be bonded to each other at a site thereof formed by removing a hydrogen atom from the substituent group.

When two selected from $R^{17}$, $R^{18}$, $R^{19}$, $R^{20}$, and $R^{21}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{17}$, $R^{18}$, $R^{19}$, $R^{20}$, and $R^{21}$ may be bonded to each other at a site thereof formed by removing a hydrogen atom from the substituent group.

$R^{10}$ in the general formula (2-1) and $R^{11}$ in the general formula (2-1) and the general formula (2-2) each independently represent a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group.

$R^{10}$ and $R^{11}$ may be bonded to each other at a site thereof formed by removing a hydrogen atom from the substituent group.]

The element of Group 4 of the periodic table of elements as $M^1$ can be a titanium atom, a zirconium atom, and a hafnium atom, and is, preferably, a titanium atom.

The halogen atom as $X^1$, $X^2$, $X^3$, $R^1$, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, and $R^{21}$ can be a fluorine atom, a chlorine atom, a bromine atom, or an iodine atom.

The hydrocarbyl group having 1 to 20 carbon atoms as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can be an alkyl group having 1 to 20 carbon atoms, an aryl group having 6 to 20 carbon atoms, and an aralkyl group having 7 to 20 carbon atoms.

The alkyl group having 1 to 20 carbon atoms can be a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, an isopentyl group, a neopentyl group, a 1-methylbutyl group, a 2-methylbutyl group, a 1-ethylpropyl group, a 1,1-dimethylpropyl group, a 1,2-dimethylpropyl group, a cyclopentyl group, an n-hexyl group, a cyclohexyl group, an n-heptyl group, an n-octyl group, an n-nonyl group, an n-decyl group, an n-undecyl group, an n-dodecyl group, an n-detradecyl group, an n-hexadecyl group, an n-octadecyl group, an n-icosyl group, and a 1-adamantyl group. The alkyl group having 1 to 20 carbon atoms is, preferably, an alkyl group having 1 to 10 carbon atoms and is, more preferably, a methyl group, an ethyl group, an isopropyl group, an n-butyl group, an isobutyl group, a sec-butyl group, a tert-butyl group, an n-pentyl group, an isopentyl group, or a neopentyl group.

The aryl group having 6 to 20 carbon atoms can be a phenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an isobutylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a naphtyl group, and an anthracenyl group. The aryl group having 6 to 20 carbon atoms is, preferably, an aryl group having 6 to 10 carbon atoms, is, more preferably, a phenyl group, a methylphenyl group, a dimethylphenyl group, or a trimethylphenyl group.

The aralkyl group having 7 to 20 carbon atoms can be a 1-methyl-1-phenylethyl group, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, a (ethylphenyl)methyl group, an (n-propylphenyl)methyl group, an (isopropylphenyl)methyl group, an (n-butylphenyl)methyl group, an (sec-butylphenyl)methyl group, a (tert-butylphenyl)methyl group, an (isobutylphenyl)methyl group, an (n-pentylphenyl)methyl group, a (neopentylphenyl)methyl group, an (n-hexylphenyl)methyl group, an (n-octylphenyl)methyl group, an (n-decylphenyl)methyl group, an (n-dodecylphenyl)methyl group, a naphthylmethyl group, and an anthracenylmethyl group. The aralkyl group having 7 to 20 carbon atoms is, preferably, an aralkyl group having 7 to 10 carbon atoms and is, more preferably, a benzyl group.

Preferably, the substituted hydrocarbyl group having 1 to 20 carbon atoms as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is a group formed by substituting at least one of the hydrogen atoms present in a hydrocarbyl group by a halogen atom. The halogen atom can be a fluorine atom, a chlorine atom, a bromine atom, and an iodine atom.

The substituted hydrocarbyl group having 1 to 20 carbon atoms can be a substituted alkyl group having 1 to 20 carbon atoms, a substituted aryl group having 6 to 20 carbon atoms, and a substituted aralkyl group having 7 to 20 carbon atoms.

The substituted alkyl group having 1 to 20 carbon atoms is, preferably, a substituted alkyl group having 1 to 10 carbon atoms that can be, for example, a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a fluoromethyl group, a perfluoropropyl group, a perfluorobutyl group, a perfluoropentyl group, and a perfluorohexyl group.

The substituted aryl group having 6 to 20 carbon atoms is, preferably, a substituted aryl group having 6 to 10 carbon atoms that can be, for example, a fluorophenyl group, a difluorophenyl group, a trifluorophenyl group, a tetrafluorophenyl group, a pentafluorophenyl group, a chlorophenyl group, a bromophenyl group, and an iodophenyl group.

The substituted aralkyl group having 7 to 20 carbon atoms is, preferably, a substituted aralkyl group having 7 to 10 carbon atoms that can be, for example, a (fluorophenyl)methyl group, a (difluorophenyl)methyl group, a (trifluorophenyl)methyl group, a (tetrafluorophenyl)methyl group, a (pentafluorophenyl)methyl group, a (chlorophenyl)methyl group, a (bromophenyl)methyl group, and an (iodophenyl)methyl group.

The hydrocarbyloxy group having 1 to 20 carbon atoms as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can be an alkoxy group having 1 to 20 carbon atoms, an aryloxy group having 6 to 20 carbon atoms, and an aralkyloxy group having 7 to 20 carbon atoms.

The alkoxy group having 1 to 20 carbon atoms can be a methoxy group, an ethoxy group, an n-propoxy group, an isopropoxy group, an n-butoxy group, a sec-butoxy group, a tert-butoxy group, an isobutoxy group, an n-pentyloxy group, a neopentyloxy group, an n-hexyloxy group, an n-octyloxy group, an n-nonyloxy group, an n-decyloxy group, an n-undecyl group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, and an n-icosyloxy group. The alkoxy group having 1 to 20 carbon atoms is, preferably, an alkoxy group having 1 to 10 carbon atoms and is, more preferably, a methoxy group, an ethoxy group, an isopropoxy group, or a tert-butoxy group.

The aryloxy group having 6 to 20 carbon atoms can be a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, an n-propylphenoxy group, an isopropylphenoxy group, an n-butylphenoxy group, a sec-butylphenoxy group, a tert-butylphenoxy group, an isobutylphenoxy group, an n-hexylphenoxy group, an n-octylphenoxy group, an n-decylphenoxy group, an n-tetradecylphenoxy group, a naphthoxy group, and an anthracenoxy group. The aryloxy group having 6 to 20 carbon atoms is, preferably an aryloxy group having 6 to 10 carbon atoms and is, more preferably, a phenoxy group, a 2-methylphenoxy group, a 3-methylphenoxy group, or a 4-methylphenoxy group.

The aralkyloxy group having 7 to 20 carbon atoms can be a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, an (n-propylphenyl)methoxy group, an (isopropylphenyl)methoxy group, an (n-butylphenyl)methoxy group, a (sec-butylphenyl)methoxy group, a (tert-butylphenyl)methoxy group, an (isobutylphenyl)methoxy group, an (n-hexylphenyl)methoxy group, an (n-octylphenyl)methoxy group, an (n-decylphenyl)methoxy group, a naphthylmethoxy group, and an anthracenylmethoxy group. The aralkyloxy group having 7 to 20 carbon atoms is, preferably, an aralkyloxy group having 7 to 10 carbon atoms and is, more preferably, a benzyloxy group.

Preferably, the substituted hydrocarbyloxy group having 1 to 20 carbon atoms as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is a substituent group formed by substituting at least one of the hydrogen atoms present in a hydrocarbyloxy group by a halogen atom. The halogen atom can be a fluorine atom, a chlorine atom, a bromine atom, and an iodine atom.

The substituted hydrocarbyloxy group having 1 to 20 carbon atoms can be a substituted alkoxy group having 1 to 20 carbon atoms, a substituted aryloxy group having 6 to 20 carbon atoms, and a substituted aralkyloxy group having 7 to 20 carbon atoms.

The substituted alkoxy group having 1 to 20 carbon atoms is, preferably, a substituted alkoxy group having 1 to 10 carbon atom(s) that can be, for example, a fluoromethoxy group, a difluoromethoxy group, a trifluoromethoxy group, a chloromethoxy group, a dichloromethoxy group, a trichloromethoxy group, a bromomethoxy group, a dibromomethoxy group, a tribromomethoxy group, a fluoroethoxy group, a perfluoropropoxy group, a perfluorobutoxy group, a perfluoropentyloxy group, and a perfluorohexyloxy group.

The substituted aryloxy group having 6 to 20 carbon atoms is, preferably, a substituted aryloxy group having 6 to 10 carbon atoms that can be, for example, a fluorophenoxy group, a difluorophenoxy group, a trifluorophenoxy group, a tetrafluorophenoxy group, a pentafluorophenoxy group, a chlorophenoxy group, a bromophenoxy group, and an iodophenoxy group.

The substituted aralkyloxy group having 7 to 20 carbon atoms is, preferably, a substituted aralkyloxy group having 7 to 10 carbon atoms that can be, for example, a (fluorophenyl)methoxy group, a (difluorophenyl)methoxy group, a (trifluorophenyl)methoxy group, a (tetrafluorophenyl)methoxy group, a (pentafluorophenyl)methoxy group, a (chlorophenyl)methoxy group, a (bromophenyl)methoxy group, and an (iodophenyl)methoxy group.

The substituted silyl group as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can be, for example, a substituent group represented by the following general formula (I).

General Formula (I): $-Si(R^{22})_3$ (The three $R^{22}$s each independently represent a hydrogen atom, a hydrocarbyl group, or a halogenated hydrocarbyl group, and the total number of the carbon atoms in the three $R^{22}$s is 1 to 20.)

The hydrocarbyl group as $R^{22}$ can be an alkyl group having 1 to 10 carbon atoms such as a methyl group, an ethyl group, an n-propyl group, an isopropyl group, an n-butyl group, a sec-butyl group, a tert-butyl group, an isobutyl group, an n-pentyl group, an n-hexyl group, a cyclohexyl group, an n-heptyl group, an n-octyl group, an n-nonyl group, and an n-decyl group; and an aryl group such as a phenyl group.

The halogenated hydrocarbyl group as $R^{22}$ is a group formed by substituting at least one of the hydrogen atoms present in the hydrocarbyl group by a halogen atom. The halogen atom can be a fluorine atom, a chlorine atom, a bromine atom, and an iodine atom.

The total number of the carbon atoms in the three $R^{22}$s is 1 to 20 and is, preferably, 3 to 18.

The substituted silyl group as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can be, for example, a methylsilyl group, an ethylsilyl group, a phenylsilyl group, and a monosubstituted silyl group such as a group formed by substituting at least one of the hydrogen atoms present in each of these substituent groups by a halogen atom; a dimethylsilyl group, a diethylsilyl group, a diphenylsilyl group, and a disubstituted silyl group such as a group formed by substituting at least one of the hydrogen atoms present in each of these substituent groups by a halogen atom; and a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a triisobutylsilyl group, a tert-butyldimethylsilyl group, a tert-butyldiphenylsilyl group, a tri-n-pentylsilyl group, a tri-n-hexylsilyl group, a tricyclohexylsilyl group, a triphenylsilyl group, and a trisubstituted silyl group such as a group formed by substituting at least one of the hydrogen atoms present in each of these substituent groups by a halogen atom. The substituted silyl group is, preferably, a trisubstituted silyl group and is, more preferably, a trimethylsilyl group, a triethylsilyl group, a tert-butyldimethylsilyl group, a triisopropylsilyl group, a triphenylsilyl group, a tert-butyldiphenylsilyl group, or a group formed by substituting at least one of the hydrogen atoms present in each of these substituent groups by a halogen atom.

The disubstituted amino group as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can be, for example, a substituent group represented by the following general formula (II).

  General Formula (II):

(The two $R^{23}$s each independently represent a hydrocarbyl group or a halogenated hydrocarbyl group, and the total number of the carbon atoms in the two $R^{23}$s is 2 to 20.)

The hydrocarbyl group or the halogenated hydrocarbyl group as $R^{23}$ can be those same as listed for the hydrocarbyl group and the halogenated hydrocarbyl group as the above $R^{22}$. The total number of the carbon atoms in the two $R^{23}$s is 2 to 20 and is, preferably, 2 to 10. The two $R^{23}$s may be bonded to each other at a site thereof formed by removing a hydrogen atom from the substituent group.

The disubstituted amino group as $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can be, for example, a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a pyrrolidinyl group, a piperidinyl group, a dihydroindolyl group, a dihydroisoindolyl group, and a group formed by substituting at least one of the hydrogen atoms present in each of these groups by a halogen atom. The disubstituted amino group is, preferably, a dimethylamino group, a diethylamino group, a pyrrolidinyl group, a piperidinyl group, or a group formed by substituting at least one of the hydrogen atoms present in each of these groups by a halogen atom.

When two selected from $R^1$, $R^2$, $R^3$, and $R^4$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^1$, $R^2$, $R^3$, and $R^4$ may be bonded to each other at a site thereof formed by removing a hydrogen atom from the substituent group.

When two selected from $R^5$, $R^6$, $R^7$, $R^8$, and $R^9$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^5$, $R^6$, $R^7$, $R^8$, and $R^9$ may be bonded to each other at a site thereof formed by removing a hydrogen atom from the substituent group.

When two selected from $R^{12}$, $R^{13}$, $R^{14}$, $R^{15}$, and $R^{16}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{12}$, $R^{13}$, $R^{14}$, $R^{15}$, and $R^{16}$ may be bonded to each other at a site thereof formed by removing a hydrogen atom from the substituent group.

When two selected from $R^{17}$, $R^{18}$, $R^{19}$, $R^{20}$, and $R^{21}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{17}$, $R^{18}$, $R^{19}$, $R^{20}$, and $R^{21}$ may be bonded to each other at a site thereof formed by removing a hydrogen atom from the substituent group. A ring formed by establishing a bond at a site formed by removing a hydrogen atom from the substituent group can be a saturated or an unsaturated hydrocarbyl ring and a saturated or an unsaturated silahydrocarbyl ring that can be, for example, a cyclopropane ring, a cyclopropene ring, a cyclobutane ring, a cyclobutene ring, a cyclopentane ring, a cyclopentene ring, a cyclohexane ring, a cyclohexene ring, a cycloheptane ring, a cycloheptene ring, a cyclooctane ring, a cyclooctene ring, a benzene ring, a naphthalene ring, an anthracene ring, a silacyclopropane ring, a silacyclobutane ring, a silacyclopentane ring, and a silacyclohexane ring. The ring may be substituted by a hydrocarbyl group having 1 to 20 carbon atoms.

$R^1$, $R^2$, $R^3$, and $R^4$ each independently are, preferably, a hydrogen atom, a halogen atom, or a hydrocarbyl group having 1 to 20 carbon atoms, are, more preferably, a hydrogen atom, a halogen atom, an alkyl group having 1 to 20 carbon atoms, an aryl group having 6 to 20 carbon atoms, or an aralkyl group having 7 to 20 carbon atoms, are, yet more preferably, an alkyl group having 1 to 20 carbon atoms, and are, most preferably, are a methyl group.

Preferably, a partial structure represented by the following general formula (2) including $R^1$, $R^2$, $R^3$, and $R^4$ is the following substance.

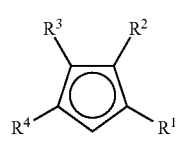

(2)

($R^1$, $R^2$, $R^3$, and $R^4$ in the general formula (2) are same as $R^1$, $R^2$, $R^3$, and $R^4$ in the general formula (2-1), the general formula (2-2), and the general formula (2-3).)

Examples of the partial structure represented by the following general formula (2) include cyclopentadienyl, methylcyclopentadienyl, ethylcyclopentadienyl, n-propylcyclopentadienyl, isopropylcyclopentadienyl, n-butylcyclopentadienyl, sec-butylcyclopentadienyl, tert-butylcyclopentadienyl, isobutylcyclopentadienyl, dimethylcyclopentadienyl, trimethylcyclopentadienyl, tetramethylcyclopentadienyl, phenylcyclopentadienyl, benzylcyclopentadienyl, indenyl, fluorenyl, tetrahydroindenyl, 2-methyltetrahydroindenyl, 3-methyltetrahydroindenyl, 2,3-dimethyltetrahydroindenyl, and octahydrofluorenyl.

More preferably, the partial structure represented by the above general formula (2) is trimethylcyclopentadienyl, tetramethylcyclopentadienyl, tetrahydroindenyl, 2-methyltetrahydroindenyl, 3-methyltetrahydroindenyl, 2,3-dimethyltetrahydroindenyl, or octahydrofluorenyl.

Preferably, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, and $R^{21}$ each independently are a hydrogen atom, a halogen atom, or a hydrocarbyl group having 1 to 20 carbon atoms.

$R^6$, $R^8$, $R^{13}$, $R^{15}$, $R^{18}$, and $R^{20}$ each are, more preferably, a substituted hydrocarbyl group having 1 to 20 carbon atoms and each are, yet more preferably, a substituted alkyl group having 1 to 20 carbon atoms.

Preferably, a partial structure represented by the following general formula (3) including $R^5$, $R^6$, $R^7$, $R^8$, and $R^9$, a partial structure represented by the following general formula (4) including $R^{12}$, $R^{13}$, $R^{14}$, $R^{15}$, and $R^{16}$, and a partial structure represented by the following general formula (5) including $R^{17}$, $R^{18}$, $R^{19}$, $R^{20}$, and $R^{21}$ each independently are the following substance.

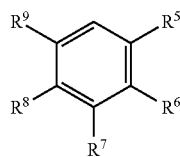

(3)

($R^5$, $R^6$, $R^7$, $R^8$, and $R^9$ in the general formula (3) are same as $R^5$, $R^6$, $R^7$, $R^8$, and $R^9$ in the general formula (2-1), the general formula (2-2), and the general formula (2-3).)

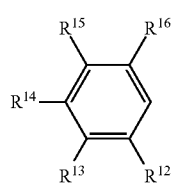

(4)

($R^{12}$, $R^{13}$, $R^{14}$, $R^{15}$, and $R^{16}$ in the general formula (4) are same as $R^{12}$, $R^{13}$, $R^{14}$, $R^{15}$, and $R^{16}$ in the general formula (2-2) and the general formula (2-3).)

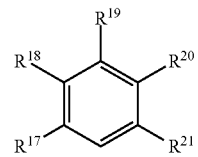

(5)

($R^{17}$, $R^{18}$, $R^{19}$, $R^{20}$, and $R^{21}$ in the general formula (5) are same as $R^{17}$, $R^{18}$, $R^{19}$, $R^{20}$, and $R^{21}$ in the general formula (2-3).)

Examples of the partial structure represented by the following general formula (3), the partial structure represented by the following general formula (4), and the partial structure represented by the following general formula (5) include phenyl, methylphenyl, dimethylphenyl, trimethylphenyl, tetramethylphenyl, pentamethylphenyl, ethylphenyl, diethylphenyl, isopropylphenyl, diisopropylphenyl, tert-butylphenyl, di-tert-butylphenyl, tert-butylmethylphenyl, di-tert-butylmethylphenyl, naphthyl, anthracenyl, chlorophenyl, dichlorophenyl, fluorophenyl, pentafluorophynyl, bis(trifluoromethyl)phenyl, biphenylyl, benzylphenyl, methoxyphenyl, phenoxyphenyl, benzyloxyphenyl, (trimethylsilyl)phenyl, and (dimethylamino)phenyl.

More preferably, the partial structure represented by the above general formula (3), the partial structure represented by the above general formula (4), and the partial structure represented by the above general formula (5) each are phenyl, methylphenyl, dimethylphenyl, trimethylphenyl, diethylphenyl, or (trimethylsilyl)phenyl. The partial structure represented by the above general formula (3), the partial structure represented by the above general formula (4), and the partial structure represented by the above general formula (5) may be same as or may be different from each other.

$R^{10}$ and $R^{11}$ each independently are, preferably, a hydrogen atom, a halogen atom, or a hydrocarbyl group having 1 to 20 carbon atoms, are, more preferably, a hydrogen atom, an alkyl group having 1 to 20 carbon atoms, or an aralkyl group having 7 to 20 carbon atoms, and are, yet more preferably, a methyl group, an ethyl group, an n-propyl group, an isopropyl group, an n-butyl group, a sec-butyl group, a tert-butyl group, an isobutyl group, or a benzyl group.

Preferably, in the general formula (2-1), a partial structure represented by the following general formula (6) including $R^{10}$ and $R^{11}$ is a following substance.

(6)

($R^{10}$ and $R^{11}$ in the general formula (6) are same as $R^{10}$ and $R^{11}$ in the general formula (2-1).)

Dimethylsilanediyl, diethylsilanediyl, ethylmethylsilanediyl, di-n-propylsilanediyl, methyl-n-propylsilanediyl, di-n-butylsilanediyl, n-butylmethylsilanediyl, n-hexylmethylsilanediyl, methyl-n-octylsilanediyl, n-decylmethylsilanediyl, methyl-n-octadecylsilanediyl, cyclohexylmethylsilanediyl, silacyclopentane-1,1-diyl, and silacyclohexan-1,1-diyl The partial structure represented by the above general formula (6) is, more preferably, a partial structure whose $R^{10}$ and $R^{11}$ are same as each other and is, yet more preferably, dimetylsilanediyl, diethylsilanediyl, silacyclopentane-1,1-diyl, or silacyclohexane-1,1-diyl.

$X^1$, $X^2$, and $X^3$ in the general formula (2-1), the general formula (2-2), and the general formula (2-3) each independently are, preferably, a halogen atom, a hydrocarbyl group having 1 to 20 carbon atoms, or a substituted hydrocarbyl group having 1 to 20 carbon atoms, are, more preferably, an alkyl group having 1 to 20 carbon atoms, a substituted alkyl group having 1 to 20 carbon atoms, an aralkyl group having 7 to 20 carbon atoms, or a substituted aralkyl group having 7 to 20 carbon atoms, and are, yet more preferably, a halogen atom, an alkyl group having 1 to 20 carbon atoms, or a substituted alkyl group having 1 to 20 carbon atoms.

The transition metal complex represented by the general formula (2-1) can be, for example, titanium chlorides as below.

(1-(dimethylphenylsilyl)-2,3,4,5-tetramethylcyclopentadienyl)trichlorotitanium, (1-(diethylphenylsilyl)-2,3,4,5-tetramethylcyclopentadienyl)trichlorotitanium, (1-(phenyldi-n-propylsilyl)-2,3,4,5-tetramethylcyclopentadienyl)trichlorotitanium, (1-/(diisopropylphenylsilyl)-2,3,4,5-tetramethylcyclopentadienyl)trichlorotitanium, (1-(di-n-butylphenylsilyl)-2,3,4,5-tetramethylcyclopentadienyl)trichlorotitanium, (1-(diisobutylphenylsilyl)-2,3,4,5-tetramethylcyclopentadienyl)trichlorotitanium, (1-(di-sec-butylphenylsilyl)-2,3,4,5-tetramethylcyclopentadienyl)trichlorotitanium, (1-(di-tert-butylphenylsiyl)-2,3,4,5-tetramethylcyclopentadienyl)trichlorotitanium, (1-(ethylmethylphenylsilyl)-2,3,4,5-tetramethylcyclopentadienyl)trichlorotitanium, (1-(methylphenyl-n-propylsilyl)-2,3,4,5-tetramethylcyclopentadienyl)trichlorotitanium, (1-(methylphenylisopropylsilyl)-2,3,4,5-tetramethylcyclopentadienyl)trichlorotitanium, (1-(n-butylmethylphenylsilyl)-2,3,4,5-tetramethylcyclopentadienyl)trichlorotitanium, (1-(isobutylmethylphenylsilyl)-2,3,4,5-tetramethylcyclopentadienyl)trichlorotitanium, (1-(sec-butylmethylphenylsilyl)-2,3,4,5-tetramethylcyclopentadienyl)trichlorotitanium, (1-(tert-butylmethylphenylsilyl)-2,3,4,5-tetramethylcyclopentadienyl)trichlorotitanium, (1-(cyclohexylmethyphenylsilyl)-2,3,4,5-tetramethylcyclopentadienyl)trichlorotitanium, and (1-(methyl-n-octadecylphenylsilyl)-2,3,4,5-tetramethylcyclopentadienyl)trichlorotitanium.

(1-(dimethyl(3,5-dimethylphenyl)silyl)-2,3,4,5-tetramethylcyclopentadienyl)trichlorotitanium, (1-(diethyl(3,5-dimethylphenylsilyl)-2,3,4,5-tetramethylcyclopentadienyl)trichlorotitanium, (1-((3,5-dimethylphenyl)di-n-propylsilyl)-2,3,4,5-tetramethylcyclopentadienyl)trichlorotitanium, (1-(diisopropyl(3,5-dimethylphenyl)silyl)-2,3,4,5-tetramethylcyclopentadienyl)-titanium, (1-(di-n-butyl(3,5-dimethylphenyl)silyl)-2,3,4,5-tetramethylcyclopentadienyl)trichlorotitanium, (1-(diisobutyl(3,5-dimethylphenyl)silyl)-2,3,4,5-tetramethylcyclopentadienyl)trichlorotitanium, (1-(di-sec-butyl(3,5-dimethylphenyl)silyl)-2,3,4,5-tetramethylcyclopentadienyl)trichlorotitanium, (1-(di-tert-butyl(3,5-dimethylphenyl)silyl)-2,3,4,5-tetramethylcyclopentadienyl)trichlorotitanium, (1-(ethylmethyl(3,5-dimethylphenyl)silyl)-2,3,4,5-tetramethylcyclopentadienyl)trichlorotitanium, (1-(methyl(3,5-dimethylphenyl)-n-propylsilyl)-2,3,4,5-tetramethylcyclopentadienyl)trichlorotitanium, (1-(methyl(3,5-dimethylphenyl)isopropylsilyl)-2,3,4,5-tetramethylcyclopentadienyl)trichlorotitanium, (1-(1-butylmethyl(3,5-dimethylphenyl)silyl)-2,3,4,5-tetramethylcyclopentadienyl)trichlorotitanium, (1-(isobutylmethyl(3,5-dimethylphenyl)silyl)-2,3,4,5-tetramethylcyclopentadienyl)trichlorotitanium, (1-(sec-butylmethyl(3,5-dimethylphenyl)silyl)-2,3,4,5-tetramethylcyclopentadienyl)trichlorotitanium, (1-(tert-butylmethyl(3,5-dimethylphenyl)silyl)-2,3,4,5-tetramethylcyclopentadienyl)trichlorotitanium, (1-(cyclohexylmethyl(3,5-dimethylphenyl)silyl)-2,3,4,5-tetramethylcyclopentadienyl)trichlorotitanium, and (1-(methyl-n-octadecyl(3,5-dimethylphenyl)silyl)-2,3,4,5-tetramethylcyclopentadienyl)trichlorotitanium.

Further examples include titanium chloride complexes formed by substituting 2,3,4,5-tetramethylcyclopentadienyl" in each of the above titanium chloride complexes by "cyclopentadienyl", "2-methylcyclopentadienyl", "3-methylcyclopentadienyl", "2,3-dimethylcyclopentadienyl", "2,4-dimethylcyclopentadienyl", "2,5-dimethylcyclopentadienyl", "2,3,5-trimethylcyclopentadienyl", "2-ethylcyclopentadienyl", "3-ethylcyclopentadienyl", "2-n-propylcyclopentadienyl", "3-n-propylcyclopentadienyl", "2-isopropylcyclopentadienyl", "3-isopropylcyclopentadienyl", "2-n-butylcyclopentadienyl" "3-n-butylcyclopentadienyl", "2-sec-butylcyclopentadienyl", "3-sec-butylcyclopentadienyl", "2-tert-butylcyclopentadienyl", "3-tert-butylcyclopentadienyl", "2-phenylcyclopentadienyl", "3-phenylcyclopentadienyl", "2-benzylcyclopentadienyl", "3-benzylcyclopentadienyl", "indenyl", "2-methylindenyl", "fluorenyl", "tetrahydroindenyl", "2-methyltetrahydroindenyl", or "octahydrofluorenyl".

Such complexes are also exemplified as transition metal chloride complexes such as zirconium chloride complexes formed by substituting "titanium" in each of the above exemplified titanium chloride complexes by "zirconium" and hafnium chloride complexes formed by substituting "titanium" therein by "hafnium", halogenated titanium complexes such as titanium fluoride complexes formed by substituting "chloro" in each of the above exemplified titanium chloride complexes by "fluoro", titanium bromide complexes formed by substituting "chloro" therein by "bromo", and titanium iodide complexes formed by substituting "chloro" therein by "iodo", alkyl-titanium complexes such as hydrogenated titanium complexes formed by substituting "chloro" in each of the above exemplified titanium chloride complexes by "hydrido" and methyl-titanium complexes formed by substituting "chloro" therein by "methyl", aryl-titanium complexes such as phenyl-titanium complexes formed by substituting "chloro" in each of the above exemplified titanium chloride complexes by "phenyl", aralkyl titanium complexes such as benzyl-titanium complexes formed by substituting "chloro" in each of the above exemplified titanium chloride complexes by "benzyl", alkoxo-titanium complexes such as methoxo-titanium complexes formed by substituting "chloro" in each of the above exemplified titanium chloride complexes by "methoxo", n-buthoxo-titanium complexes formed by substituting "chloro" therein by "n-buthoxo", and isopropoxo-titanium complexes formed by substituting "chloro" therein by "isopropoxo", aryloxo-titanium complexes such as phenoxo-titanium complexes formed by substituting "chloro" in each of the above exemplified titanium chloride complexes by "phenoxo", aralkyloxo-titanium complexes such as benzyloxo-titanium complexes formed by substituting "chloro" in each of the above exemplified titanium chloride complexes by "benzyloxo", and amido-titanium complexes such as dimethylamido-titanium complexes formed by substituting "chloro" in each of the above exemplified titanium chloride complexes by "dimethylamido", and diethylamido-titanium complexes formed by substituting "chloro" therein by "diethylamido".

The transition metal complex represented by the general formula (2-2) can be, for example, the following titanium chloride complexes.

(1-(methyldiphenylsilyl)-2,3,4,5-tetramethylcyclopentadienyl)trichlorotitanium, (1-(ethyldiphenylsilyl)-2,3,4,5-tetramethylcyclopentadienyl)trichlorotitanium, (1-(n-propyldiphenylsilyl)-2,3,4,5-tetramethylcyclopentadienyl)trichlorotitanium, (1-(isopropyldiphenylsilyl)-2,3,4,5-tetramethylcyclopentadienyl)trichlorotitanium, (1-(n-butyldiphenylsilyl)-2,3,4,5-tetramethylcyclopentadienyl)trichlorotitanium, (1-(isobutyldiphenylsilyl)-2,3,4,5-tetramethylcyclopentadienyl)trichlorotitanium, (1-sec-butyldiphenylslyl)-2,3,4,5-tetramethylcyclopentadienyl)trichlorotitanium, (1-(tert-butyldiphenylsilyl)-2,3,4,5-tetramethylcyclopentadienyl)trichlorotitanium, (1-(cyclohexyldiphenylsilyl)-2,3,4,5-tetramethylcyclopentadienyl)trichlorotitanium, (1-(n-oetadecyldiphenylsilyl)-2,3,4,5-tetramethylcyclopentadienyl)trichlorotitanium, (1-(methylphenyl(2-methylphenyl)silyl)-2,3,4,5-tetramethylcyclopentadienyl)trichlorotitanium, (1-(methylphenyl(3-methylphenyl)silyl)-2,3,4,5-tetramethylcyclopentadienyl)trichlorotitanium, (1-(methylphenyl(4-methylphenyl)silyl)-2,3,4,5-tetramethylcyclopentadienyl)trichlorotitanium, (1-(methylphenyl(2,3-dimethylphenyl)silyl)-2,3,4,5-tetramethylcyclopentadienyl)trichlorotitanium, (1-(methylphenyl(2,4-dimethylphenyl)silyl)-2,3,4,5-tetramethylcyclopentadienyl)trichlorotitanium, (1-(methylphenyl(2,5-di ethylphenyl)silyl)-2,3,4,5-tetramethylcyclopentadienyl)trichlorotitanium, (1-(methylphenyl(2,6-dimethylphenyl)silyl)-2,3,4,5-tetramethylcyclopentadienyl)trichlorotitanium, (1-(methylphenyl(3,5-dimethylphenyl)silyl)-2,3,4,5-tetramethylcyclopentadienyl)trichlorotitanium, and (1-(methylphenyl(3,4,5-trimethylphenyl)silyl)-2,3,4,5-tetramethylcyclopentadienyl)trichlorotitanium.

(1-(ethylphenyl(3,5-dimethylphenyl)silyl)-2,3,4,5-tetramethylcyclopentadienyl)trichlorotitanium, (1-(n-propylphenyl(3,5-dimethylphenyl)silyl)-2,3,4,5-tetramethylcyclopentadienyl)trichlorotitanium, (1-(isopropylphenyl(3,5-dimethylphenyl)silyl)-2,3,4,5-tetramethylcyclopentadienyl)trichlorotitanium, (1-(n-butylphenyl(3,5-dimethylphenyl)silyl)-2,3,4,5-tetramethylcyclopentadienyl)trichlorotitanium, (1-(isobutylphenyl(3,5-dimethylphenyl)silyl)-2,3,4,5-tetramethylcyclopentadienyl)trichlorotitanium, (1-(sec-butylphenyl(3,5-dimethylphenyl)silyl)-2,3,4,5-tetramethylcyclopentadienyl)trichlorotitanium, (1-(tert-butylphenyl(3,5-dimethylphenyl)silyl)-2,3,4,5-tetramethylcyclopentadienyl)trichlorotitanium, (1-(cyclohexylphenyl(3,5-dimethylphenyl)silyl)-2,3,4,5-tetramethylcyclopentadienyl)trichlorotitanium, (1-(n-octadecylphenyl(3,5-dimethylphenyl)silyl)-2,3,4,5-tetramethylcyclopentadienyl)trichlorotitanium, (1-(methyl(2-methylphenyl)(3,5-dimethylphenyl)silyl)-2,3,4,5-tetramethylcyclopentadienyl)trichlorotitanium, (1-(methyl(3-methylphenyl)(3,5-dimethylphenyl)silyl)-2,3,4,5-tetramethylcyclopentadienyl)trichlorotitanium, (1-(methyl(4-methyl phenyl)(3,5-dimethylphenyl)silyl)-2,3,4,5-tetramethylcyclopentadienyl)trichlorotitanium, (1-(methyl(2,3-dimethylphenyl)(3,5-dimethylphenyl)silyl)-2,3,4,5-tetramethylcyclopentadienyl)trichlorotitanium, (1-(methyl(2,4-dimethylphenyl)(3,5-dimethylphenyl)silyl)-2,3,4,5-tetra ethylcyclopentadienyl)trichlorotitanium, (1-(methyl(2,5-dimethylphenyl)(3,5-dimethylphenyl)silyl)-2,4,5-tetramethylcyclopentadienyl)trichlorotitanium, (1-(methyl(2,6-dimethylphenyl)(3,5-dimethylphenyl)silyl)-2,3,4,5-tetramethylcyclopentadienyl)trichlorotitanium, (1-(1 ethylbis(3,5-dimethylphenyl)silyl)-2,3,4,5-tetramethylcyclopentadienyl)trichlorotitanium, and (1-(methyl(3,5-dimethylphenyl)(3,4,5-trimethylphenyl)silyl)-2,3,4,5-tetramethylcyclopentadienyl)trichlorotitanium.

Such titanium chloride complexes are also exemplified as those formed by substituting "2,3,4,5-tetramethylcyclopentadienyl" in the above titanium chloride complexes by "cyclopentadienyl", "2-methylcyclopentadienyl", "3-methylcyclopentadienyl", "2,3-dimethylcyclopentadienyl", "2,4-dimethylcyclopentadienyl", "2,5-dimethylcyclopentadienyl", "2,3,5-trimethylcyclopentadienyl", "2-ethylcyclopentadienyl", "3-ethylcyclopentadienyl", "2-n-propylcyclopentadienyl", "3-n-propylcyclopentadienyl", "2-isopropylcyclopentadienyl", "3-isopropylcyclopentadienyl", "2-n-butylcyclopentadienyl", "3-n-butylcyclopentadienyl" "2-sec-butylcyclopentadienyl", "3-sec-butylcyclopentadienyl", "2-tert-butylcyclopentadienyl" "3-tert-butylcyclopentadienyl", "2-phenylcyclopentadienyl", "3-phenylcyclopentadienyl", "2-benzylcyclopentadienyl", "3-benzylcyclopentadienyl", "indenyl", "2-methylindenyl", "fluorenyl", "tetrahydroindenyl", "2-methyltetrahydroindenyl", or "octahydrofluorenyl".

Such complexes are also exemplified as, transition metal chloride complexes such as zirconium chloride complexes formed by substituting "titanium" in each of the above exemplified titanium chloride complexes by "zirconium" and hafnium chloride complexes formed by substituting "titanium" therein by "hafnium", halogenated titanium complexes such as titanium fluoride complexes formed by substituting "chloro" in each of the above exemplified titanium chloride complexes by "fluoro", titanium bromide complexes formed by substituting "chloro" therein by "bromo", and titanium iodide complexes formed by substituting "chloro" therein by "iodo", alkyl-titanium complexes such as hydrogenated titanium complexes formed by substituting "chloro" in each of the above exemplified titanium chloride complexes by "hydrido" and methyl-titanium complexes formed by substituting "chloro" therein by "methyl", aryl-titanium complexes such as phenyl-titanium complexes formed by substituting "chloro" in each of the above exemplified titanium chloride complexes by "phenyl", aralkyl titanium complexes such as benzyl-titanium complexes formed by substituting "chloro" in each of the above exemplified titanium chloride complexes by "benzyl", alkoxo-titanium complexes such as methoxo-titanium complexes formed by substituting "chloro" in each of the above exemplified titanium chloride complexes by "methoxo", n-buthoxo-titanium complexes formed by substituting "chloro" therein by "n-buthoxo", and isopropoxo-titanium complexes formed by substituting "chloro" therein by "isopropoxo", aryloxo-titanium complexes such as phenoxo-titanium complexes formed by substituting "chloro" in each of the above exemplified titanium chloride complexes by "phenoxo", aralkyloxo-titanium complexes such as benzyloxo-titanium complexes formed by substituting "chloro" in each of the above exemplified titanium chloride complexes by "benzyloxo", and amido-titanium complexes such as dimethylamido-titanium complexes formed by substituting "chloro" in each of the above exemplified titanium chloride complexes by "dimethylamido", and diethylamido-titanium complexes formed by substituting "chloro" therein by "diethylamido".

The transition metal complex represented by the general formula (2-3) can be, for example, the following titanium chloride complexes.

(1-(triphenylsilyl)-2,3,4,5-tetramethylcyclopentadienyl) trichlorotitanium, (1-(phenylbis(2-methylphenyl)silyl)-2,3,4,5-tetramethylcyclopentadienyl)trichlorotitanium, (1-(phenylbis(3-methylphenyl)silyl)-2,3,4,5-tetramethylcyclopentadienyl)trichlorotitanium, (1-(phenylbis(4-methylphenyl)silyl)-2,3,4,5-tetramethylcyclopentadienyl)trichlorotitanium, (1-(phenylbis(2,3-dimethylphenyl)silyl)-2,3,4,5-tetramethylcyclopentadienyl)trichlorotitanium, (1-(phenylbis(2,4-dimethylphenyl)silyl)-2,3,4,5-tetramethylcyclopentadienyl)trichlorotitanium, (1-(phenylbis(2,5-dimethyl phenyl)silyl)-2,3,4,5-tetramethylcyclopentadienyl)trichlorotitanium, (1-(phenylbis(2,6-dimethylphenyl)silyl)-2,3,4,5-tetramethylcyclopentadienyl)trichlorotitanium, (1-(phenylbis(3,5-dimethylphenyl)silyl)-2,3,4,5-tetramethylcyclopentadienyl)trichlorotitanium, and (1-(phenylbis(3,4,5-trimethylphenyl)silyl)-2,3,4,5-tetramethylcyclopentadienyl)trichlorotitanium.

(1-(diphenyl(2-methylphenyl)silyl)-2,3,4,5-tetramethylcyclopentadienyl)trichlorotitanium, (1-(diphenyl(3-methylphenyl)silyl)-2,3,4,5-tetramethylcyclopentadienyl)trichlorotitanium, (1-(diphenyl(4-methylphenyl)silyl)-2,3,4,5-tetramethylcyclopentadienyl)trichlorotitanium, (1-(diphenyl(2,3-dimethylphenyl)silyl)-2,3,4,5-tetramethylcyclopentadienyl)trichlorotitanium, (1-(diphenyl(2,4-dimethylphenyl)silyl)-2,3,4,5-tetramethylcyclopentadienyl)trichlorotitanium, (1-(diphenyl(2,5-dimethylphenyl)silyl)-2,3,4,5-tetramethylcyclopentadienyl)trichlorotitanium, (1-(diphenyl(2,6-dimethylphenyl)silyl)-2,3,4,5-tetramethylcyclopentadienyl)trichlorotitanium, (1-(diphenyl(3,5-dimethylphenyl)silyl)-2,3,4,5-tetramethylcyclopentadienyl)trichlorotitanium, and (1-(diphenyl(3,4,5-trimethylphenyl)silyl)-2,3,4,5-tetramethylcyclopentadienyl)trichlorotitanium.

(1-(phenyl(2-methylphenyl)(3,5-dimethylphenyl)silyl)-2,3,4,5-tetramethylcyclopentadienyl)trichlorotitanium, (1-(phenyl(3-methylphenyl)(3,5-dim ethylphenyl)silyl)-2,3,4,5-tetramethylcyclopentadienyl)trichlorotitanium, (1-(phenyl(4-methylphenyl)(3,5-dimethylphenyl)silyl)-2,3,4,5-tetramethylcyclopentadienyl)trichlorotitanium, (1-(phenyl(2,3-dimethylphenyl)(3,5-dimethylphenyl)silyl)-2,3,4,5-tetramethylcyclopentadienyl)trichlorotitanium, (1-(phenyl(2,4-dimethylphenyl)(3,5-dimethylphenyl)silyl)-2,3,4,5-tetramethylcyclopentadienyl)trichlorotitanium, (1-(phenyl(2,5-dimethylphenyl)(3,5-dimethylphenyl)silyl)-2,3,4,5-tetramethylcyclopentadienyl)trichlorotitanium, (1-phenyl(2,6-dimethylphenyl)(3,5-dimethylphenyl)silyl)-2,3,4,5-tetramethylcyclopentadienyl)trichlorotitanium, and (1-(phenyl(3,5-dimethylphenyl)(3,4,5-trimethylphenyl)silyl)-2,3,4,5-tetramethylcyclopentadienyl)trichlorotitanium.

(1-(bis(2-methylphenyl)(3,5-dimethylphenyl)silyl)-2,3,4,5-tetramethylcyclopentadienyl)trichlorotitanium, (1-(bis(3-methylphenyl)(3,5-dimethylphenyl)silyl)-2,3,4,5-tetramethylcyclopentadienyl)trichlorotitanium, (1-(bis(4-methylphenyl)(3,5-dimethylphenyl)silyl)-2,3,4,5-tetramethylcyclopentadienyl)trichlorotitanium, (1-(bis(2,3-dimethylphenyl)(3,5-dimethylphenyl)silyl)-2,3,4,5-tetramethylcyclopentadienyl)trichlorotitanium, (1-(bis(2,4-dimethylphenyl)(3,5-dimethylphenyl)silyl)-2,3,4,5-tetramethylcyclopentadienyl)trichlorotitanium, (1-(bis(2,5-dimethylphenyl)(3,5-dimethylphenyl)silyl)-2,3,4,5-tetramethylcyclopentadienyl)trichlorotitanium, (1-(bis(2,6-dimethylphenyl)(3,5-dimethylphenyl)silyl)-2,3,4,5-tetramethylcyclopentadienyl)trichlorotitanium, (1-(tris(3,5-di methylphenyl)silyl)-2,3,4,5-tetramethyl cyclopentadienyl)trichlorotitanium, and (1-((3,5-dimethylphenyl)bis(3,4,5-dimethylphenyl)silyl)-2,3,4,5-tetramethylcyclopentadienyl)trichlorotitanium.

Such titanium chloride complexes are also exemplified as those formed by substituting "2,3,4,5-tetramethylcyclopentadienyl" in the above titanium chloride complexes by "cyclopentadienyl", "2-methylcyclopentadienyl", "3-methylcyclopentadienyl", "2,3-dimethylcyclopentadienyl", "2,4-dimethylcyclopentadienyl", "2,5-dimethylcyclopentadienyl", "2,3,5-trimethylcyclopentadienyl", "2-ethylcyclopentadienyl", "3-ethylcyclopentadienyl", "2-n-propylcyclopentadienyl", "3-n-propylcyclopentadienyl", "2-isopropylcyclopentadienyl", "3-isopropylcyclopentadienyl", "2-n-butylcyclopentadienyl", "3-n-butylcyclopentadienyl", "2-sec-butylcyclopentadienyl", "3-sec-butylcyclopentadienyl", "2-tert-butylcyclopentadienyl", "3-tert-butylcyclopentadienyl", "2-phenylcyclopentadienyl", "3-phenylcyclopentadienyl", "2-benzylcyclopentadienyl", "3-benzylcyclopentadienyl", "indenyl", "2-methylindenyl", "fluorenyl", "tetrahydroindenyl", "2-methyltetrahydroindenyl", or "octahydrofluorenyl".

Such complexes are also exemplified as transition metal chloride complexes such as zirconium chloride complexes formed by substituting "titanium" in each of the above exemplified titanium chloride complexes by "zirconium" and hafnium chloride complexes formed by substituting "titanium" therein by "hafnium", halogenated titanium complexes such as titanium fluoride complexes formed by substituting "chloro" in each of the above exemplified titanium chloride complexes by "fluoro", titanium bromide complexes formed by substituting "chloro" therein by "bromo", and titanium iodide complexes formed by substituting "chloro" therein by "iodo", alkyl-titanium complexes such as hydrogenated titanium complexes formed by substituting "chloro" in each of the above exemplified titanium chloride complexes by "hydrido" and methyl-titanium complexes formed by substituting "chloro" therein by "methyl", aryl-titanium complexes such as phenyl-titanium complexes formed by substituting "chloro" in each of the above exemplified titanium chloride complexes by "phenyl", aralkyl titanium complexes such as benzyl-titanium complexes formed by substituting "chloro" in each of the above exemplified titanium chloride complexes by "benzyl", alkoxo-titanium complexes such as methoxo-titanium complexes formed by substituting "chloro" in each of the above exemplified titanium chloride complexes by "methoxo", n-buthoxo-titanium complexes formed by substituting "chloro" therein by "n-buthoxo", and isopropoxo-titanium complexes formed by substituting "chloro" therein by "isopropoxo", aryloxo-titanium complexes such as phenoxo-titanium complexes formed by substituting "chloro" in each of the above exemplified titanium chloride complexes by "phenoxo", aralkyloxo-titanium complexes such as benzyloxo-titanium complexes formed by substituting "chloro" in each of the above exemplified titanium chloride complexes by "benzyloxo", and amido-titanium complexes such as dimethylamido-titanium complexes formed by substituting "chloro" in each of the above exemplified titanium chloride complexes by "dimethylamido", and diethylamido-titanium complexes formed by substituting "chloro" therein by "diethylamido".

The production method of the transition metal complexes represented by the general formula (2-1), (2-2), or (2-3) can be methods described in Japanese Laid-Open Patent Publication Nos. 2011-98954 and 2013-184926.

The transition metal complex represented by a general formula (2-4) and the transition metal complex represented by a general formula (2-5) will be described in detail.

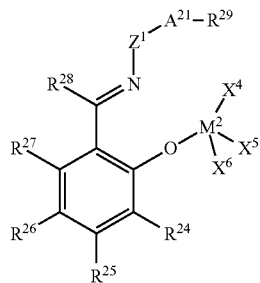

(2-4)

[$M^2$ in the general formula (2-4) represents a transition metal atom of Group 4 of the periodic table of the elements.

$A^{21}$ represents an oxygen atom, a nitrogen atom, a phosphorus atom, or a sulfur atom. $Z^1$ represents a group linking $A^{21}$ and N to each other and the smallest number of the bonds linking $A^{21}$ and N to each other is 4 to 6. The bond linking $A^{21}$ and $Z^1$ to each other may be a double bond.

$R^{24}$, $R^{25}$, $R^{26}$, $R^{27}$, $R^{28}$, $X^4$, $X^5$, and $X^6$ each independently represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group.

When two selected from $R^{24}$, $R^{25}$, $R^{26}$, $R^{27}$, and $R^{28}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{24}$, $R^{25}$, $R^{26}$, $R^{27}$, and $R^{28}$ may be bonded to each other at a site thereof formed by removing a hydrogen atom from the substituent group.

$R^{29}$ represents a hydrogen atom, a halogen atom, a hydrocarbyl group having 1 to 20 carbon atoms, a substituted hydrocarbyl group having 1 to 20 carbon atoms, a hydrocarbylidene group having 1 to 20 carbon atoms, or a substituted hydrocarbylidene group having 1 to 20 carbon atoms. The bond linking $R^{29}$ and $A^{21}$ to each other may be a double bond. $R^{29}$ may be bonded to $Z^1$.]

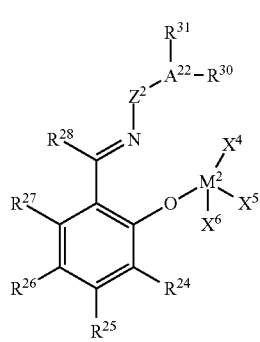

(2-5)

[$M^2$ in the general formula (2-5) represents a transition metal atom of Group 4 of the periodic table of the elements.

$A^{22}$ represents a nitrogen atom or a phosphorus atom. $Z^2$ represents a group linking $A^{22}$ and N to each other and the smallest number of the bonds linking $A^{22}$ and N to each other is 4 to 6.

$R^{24}$, $R^{25}$, $R^{26}$, $R^{27}$, $R^{28}$, $X^4$, $X^5$, and $X^6$ each independently represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group.

When two selected from $R^{24}$, $R^{25}$, $R^{26}$, $R^{27}$, and $R^{28}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{24}$, $R^{25}$, $R^{26}$, $R^{27}$, and $R^{28}$ may be bonded to each other at a site thereof formed by removing a hydrogen atom from the substituent group.

$R^{30}$ and $R^{31}$ each represent a hydrogen atom, a halogen atom, a hydrocarbyl group having 1 to 20 carbon atoms, or a substituted hydrocarbyl group having 1 to 20 carbon atoms. $R^{30}$ or $R^{31}$ may be bonded to $Z^2$.]

$M^2$ can be a titanium atom, a zirconium atom, and a hafnium atom, and is, preferably, a titanium atom.

$R^{24}$, $R^{25}$, $R^{26}$, $R^{27}$, $R^{28}$, $X^4$, $X^5$, and $X^6$ each represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group. The definitions and examples of these atoms or substituent groups are same as those described for the hydrogen atom, the halogen atom, the hydrocarbyl group having 1 to 20 carbon atoms, the substituted hydrocarbyl group having 1 to 20 carbon atoms, the hydrocarbyloxy group having 1 to 20 carbon atoms, the substituted hydrocarbyloxy group having 1 to 20 carbon atoms, the substituted silyl group, or the disubstituted amino group as the above $X^1$, $X^2$, $X^3$, $R^1$, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, and $R^{21}$.

Preferably, the number of carbon atom(s) of each of the hydrocarbyl group, the substituted hydrocarbyl group, the hydrocarbyloxy group, and the substituted hydrocarbyloxy group as $R^{24}$, $R^{25}$, $R^{26}$, $R^{27}$, $R^{28}$, $X^4$, $X^5$, and $X^6$ is 1 to 10.

Preferably, the substituted silyl group as $R^{24}$, $R^{25}$, $R^{27}$, $R^{28}$, $X^4$, $X^5$, and $X^6$ is a trisubstituted silyl group and, preferably, the number of carbon atom(s) in the hydrocarbyl group or the halogenated hydrocarbyl group bonded to a silicon atom is 1 to 10. In the substituted silyl group, preferably, the total of the number of carbon atoms in the hydrocarbyl group or the halogenated hydrocarbyl group bonded to a silicon atom is 3 to 18. More preferably, the substituted silyl group as $R^{24}$, $R^{25}$, $R^{26}$, $R^{27}$, $R^{28}$, $X^4$, $X^5$, and $X^6$ is a trimethylsilyl group, a triethylsilyl group, a triphenylsilyl group, a dimethylphenylsilyl group, or a substituent group formed by substituting at least one of the hydrogen atoms present in each of these substituent groups by a halogen atom.

In the disubstituted amino group as $R^{24}$, $R^{25}$, $R^{26}$, $R^{27}$, $R^{28}$, $X^4$, $X^5$, and $X^6$, the number of carbon atom(s) in the hydrocarbyl group or the halogenated hydrocarbyl group bonded to a nitrogen atom is, preferably, 1 to 10 and is, more preferably, 1 to 5. Preferably, the total of the number of carbon atoms in the hydrocarbyl group or the halogenated hydrocarbyl group bonded to a nitrogen atom is 2 to 10.

When two selected from $R^{24}$, $R^{25}$, $R^{26}$, $R^{27}$, and $R^{28}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{24}$, $R^{25}$, $R^{26}$, $R^{27}$, and $R^{28}$ may be bonded to each other at a site thereof formed by removing a hydrogen atom from the substituent group. A ring formed by establishing a bond at a site formed by removing a hydrogen atom from the substituent group can be a saturated or an unsaturated hydrocarbyl ring such as a cyclopropane ring, a cyclopropene ring, a cyclobutane ring, a cyclobutene ring, a cyclopentane ring, a cyclopentene ring, a cyclohexane ring, a cyclohexene ring, a cycloheptane ring, a cycloheptene ring, a cyclooctane ring, a cyclooctene ring, a benzene ring, a naphthalene ring, and an anthracene ring. At least one of the hydrogen atoms on the ring may be substituted by a hydrocarbyl group having 1 to 20 carbon atoms.

$R^{24}$ is, more preferably, a phenyl group, a 1-methyl-1-phenylethyl group, a tert-butyl group, or a 1-adamantyl group and is, yet more preferably, a 1-adamantyl group.

$R^{26}$ is, more preferably, a methyl group, a cyclohexyl group, a tert-butyl group, or a 1-adamantyl group and is, yet more preferably, a methyl group.

More preferably, $R^{25}$, $R^{27}$, and $R^{28}$ each are a hydrogen atom.

$X^4$, $X^5$, and $X^6$ each are, more preferably, a halogen atom or an alkyl group having 1 to 10 carbon atoms and each are, yet more preferably, a chlorine atom, a bromine atom, or a methyl group.

$A^{21}$ represents an oxygen atom, a nitrogen atom, a phosphorus atom, or a sulfur atom. $A^{22}$ represents a nitrogen atom or a phosphorus atom.

$R^{29}$ represents a hydrogen atom, a halogen atom, a hydrocarbyl group having 1 to 20 carbon atoms, a substituted hydrocarbyl group having 1 to 20 carbon atoms, a hydrocarbylidene group having 1 to 20 carbon atoms, or a substituted hydrocarbylidene group having 1 to 20 carbon atoms. The bond linking $R^{29}$ and $A^{21}$ may be a double bond. The definitions and examples of the halogen atom, the hydrocarbyl group having 1 to 20 carbon atoms, or the substituted hydrocarbyl group having 1 to 20 carbon atoms are same as those described for the halogen atom, the hydrocarbyl group having 1 to 20 carbon atoms, or the substituted hydrocarbyl group having 1 to 20 carbon atoms as the above $X^1$, $X^2$, $X^3$, $R^1$, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, and $R^{21}$.

The hydrocarbylidene group having 1 to 20 carbon atoms can be a methylidene group, an ethylidene group, a benzylidene group, and a cyclohexylidene group. The substituted hydrocarbylidene group having 1 to 20 carbon atoms can be, for example, a substituent group formed by substituting at least one of the hydrogen atoms present in the hydrocarbyl group having 1 to 20 carbon atoms by a halogen atom. The halogen atom can be a fluorine atom, a chlorine atom, a bromine atom, and an iodine atom.

In $R^{29}$, the number of carbon atoms of each of the hydrocarbyl group, the substituted hydrocarbyl group, the hydrocarbylidene group, and the substituted hydrocarbylidene group is, preferably, 1 to 10 and is, more preferably, 1 to 5.

$R^{29}$ is, preferably, a hydrocarbyl group having 1 to 5 carbon atoms, is, more preferably, a methyl group, an ethyl group, or an isopropyl group, and is, yet more preferably, a methyl group.

$R^{30}$ and $R^{31}$ each represent a hydrogen atom, a halogen atom, a hydrocarbyl group having 1 to 20 carbon atoms, and a substituted hydrocarbyl group having 1 to 20 carbon atoms. The meanings and examples of the halogen atom, the hydrocarbyl group having 1 to 20 carbon atoms, or the substituted hydrocarbyl group having 1 to 20 carbon atoms as $R^{30}$ and $R^{31}$ are same as those described for the halogen atom, the hydrocarbyl group having 1 to 20 carbon atoms, or the substituted hydrocarbyl group having 1 to 20 carbon atoms as the above $X^1$, $X^2$, $X^3$, $R^1$, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, and $R^{21}$.

The number of carbon atoms of each of the hydrocarbyl group and the substituted hydrocarbyl group as $R^{30}$, and $R^{31}$ is, preferably, 1 to 10 and is, more preferably, 1 to 5.

$R^{30}$ is, preferably, a hydrocarbyl group having one or more and five or less carbon atom(s), is, more preferably, a methyl group, an ethyl group, or an isopropyl group, and is, yet more preferably, a methyl group.

$R^{31}$ is, preferably, a hydrocarbyl group having 1 to 5 carbon atoms, is, more preferably, a methyl group, an ethyl group, or an isopropyl group, and is, yet more preferably, a methyl group.

$Z^1$ represents a group linking $A^{21}$ and N to each other and the number of shortest bonds linking $A^{21}$ and N to each other is 4 to 6. The bond linking $A^{21}$ and $Z^1$ to each other may be a double bond. $Z^2$ represents a group linking $A^{22}$ and N to each other and the number of shortest bonds linking $A^{22}$ and N to each other is 4 to 6. The number of shortest bonds is defined using a method described in WO 2009-005003.

$Z^1$ and $Z^2$ each can be the structure represented by the following general formula (7). The carbon atom bonded to $R^{32}$ in the following general formula (7) bonds to a nitrogen atom in the general formula (2-4) or the general formula (2-5) and the carbon atom bonded to $R^{35}$ bonds to $A^{21}$ in the general formula (2-4) or $A^{22}$ in the general formula (2-5).

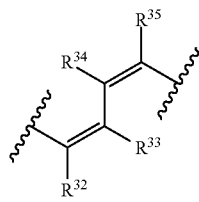

(7)

[$R^{32}$, $R^{33}$, $R^{34}$, and $R^{35}$ in the general formula (7) each represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms. When $R^{32}$ and $R^{33}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, $R^{32}$ and $R^{33}$ may be bonded to each other at a site thereof formed by removing a hydrogen atom from the substituent group. When $R^{34}$ and $R^{35}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, $R^{34}$ and $R^{35}$ may be bonded to each other at a site thereof formed by removing a hydrogen atom from the substituent group.]

When $R^{35}$ is a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, and $R^{29}$ in the general formula (2-4) or $R^{31}$ in the general formula (2-5) is a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, $R^{35}$ and $R^{29}$, or $R^{35}$ and $R^{31}$ may be bonded to each other at a site thereof formed by removing a hydrogen atom from the substituent group.

The definitions and examples of the hydrocarbyl group having 1 to 20 carbon atoms, the substituted hydrocarbyl group having 1 to 20 carbon atoms, the hydrocarbyloxy group having 1 to 20 carbon atoms, and the substituted hydrocarbyloxy group having 1 to 20 carbon atoms as $R^{32}$, $R^{33}$, $R^{34}$, and $R^{35}$ are same as those described for the hydrocarbyl group having 1 to 20 carbon atoms, the substituted hydrocarbyl group having 1 to 20 carbon atoms, the hydrocarbyloxy group having 1 to 20 carbon atoms, and the substituted hydrocarbyloxy group having 1 to 20 carbon atoms as the above $X^1$, $X^2$, $X^3$, $R^1$, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, and $R^{21}$.

Preferably, the number of carbon atom(s) of the hydrocarbyl group, the substituted hydrocarbyl group, the hydrocarbyloxy group, and the substituted hydrocarbyloxy group as $R^{32}$, $R^{33}$, $R^{34}$, and $R^{35}$ is 1 to 10.

The production method of the transition metal complex represented by the general formula (2-4) or the transition metal complex represented by the general formula (2-5) can be the method described in WO 2009-005003.

The transition metal complex represented by the general formula (2-4) or the transition metal complex represented by the general formula (2-5) can be, for example, the following compounds.

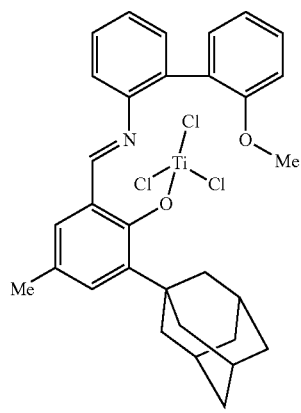

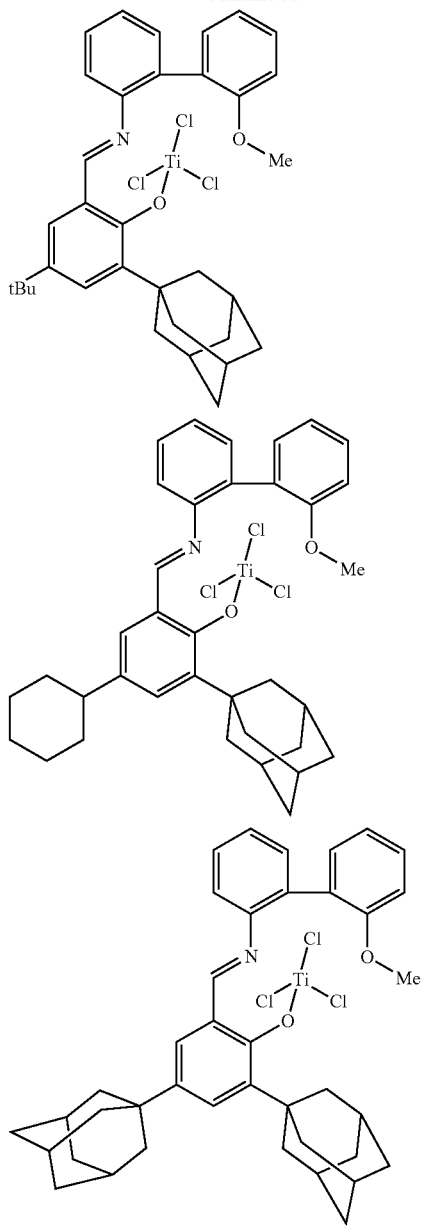

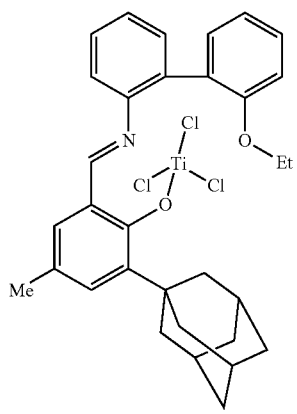

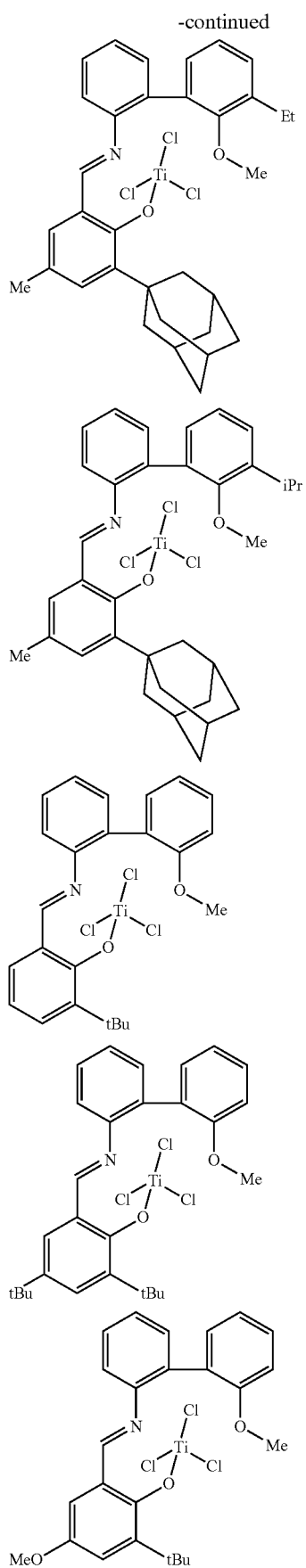
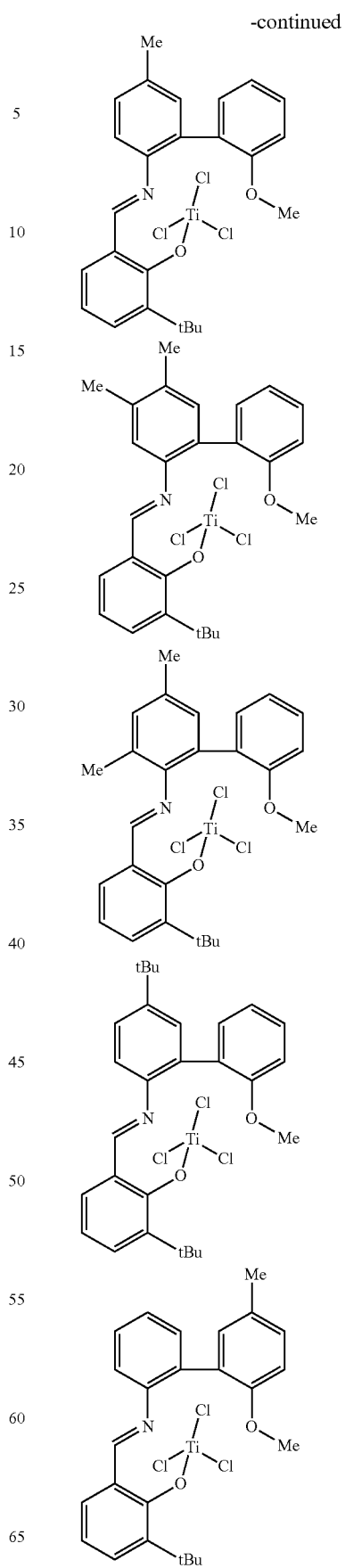

31
-continued
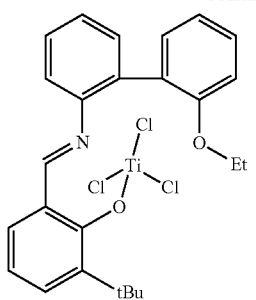
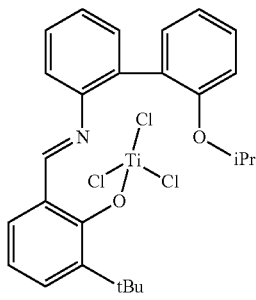
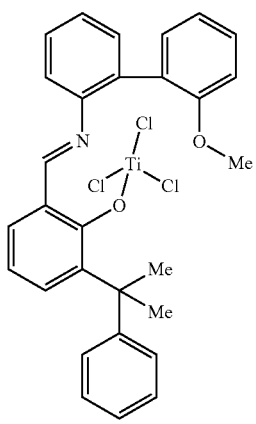
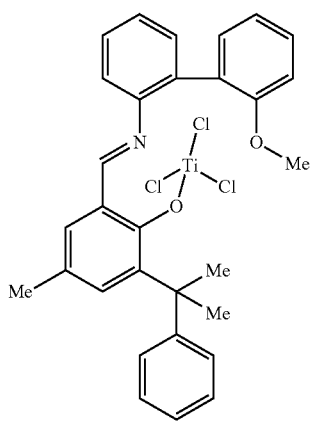
32
-continued
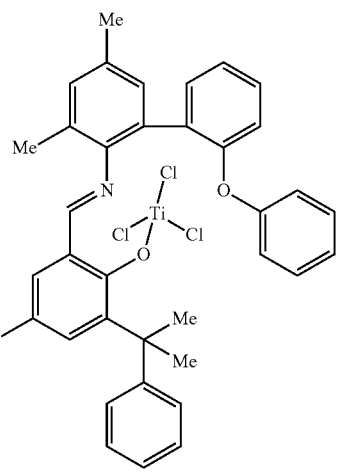
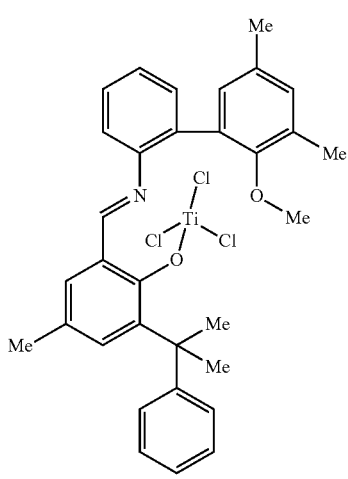
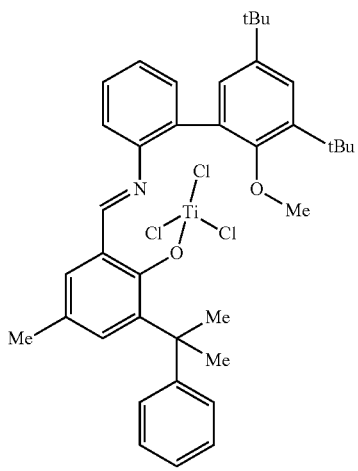

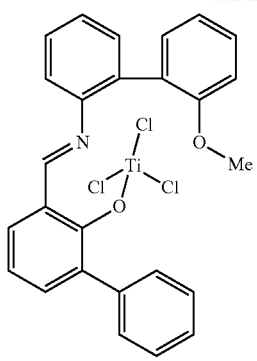

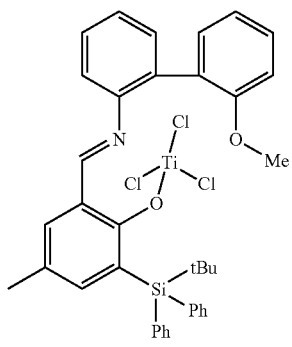

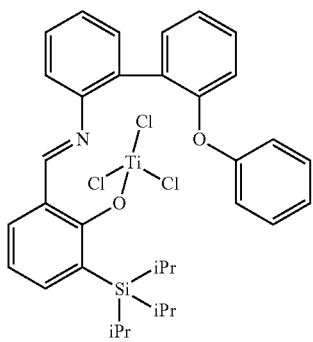

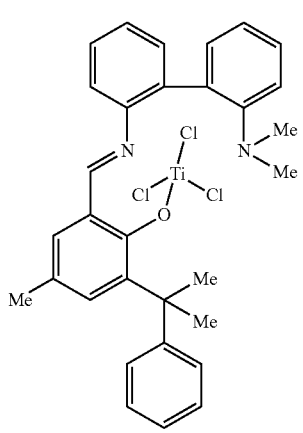

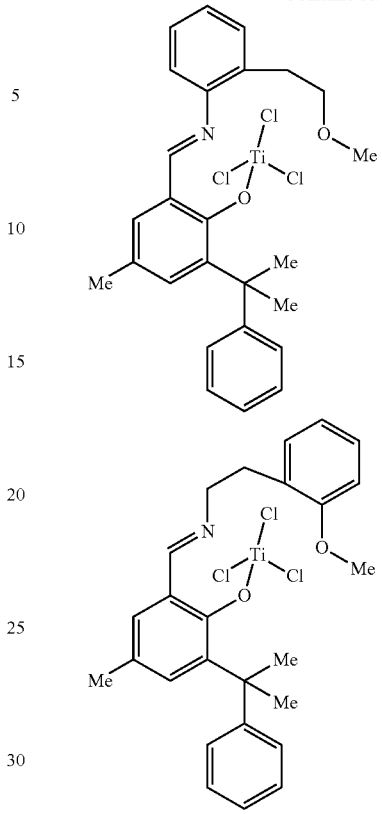

Preferably, the transition metal complex represented by the general formula (2-4) or the transition metal complex represented by the general formula (2-5) can be the transition metal complex represented by the following general formula (2-a) or the general formula (2-b).

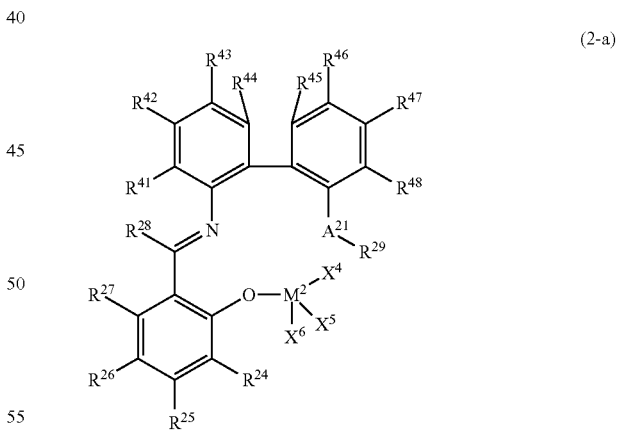

[$M^2$, $A^{21}$, $R^{24}$, $R^{25}$, $R^{26}$, $R^{27}$, $R^{28}$, $X^4$, $X^5$, and $X^6$ in the general formula (2-a) are respectively same as the above $M^2$, $A^{21}$, $R^{24}$, $R^{25}$, $R^{26}$, $R^{27}$, $R^{28}$, $X^4$, $X^5$, and $X^6$.

Two selected from $R^{24}$, $R^{25}$, $R^{26}$, $R^{27}$, and $R^{28}$ may be bonded to each other at a site thereof formed by removing a hydrogen atom from the substituent group. $X^4$, $X^5$, and $X^6$ may be same as or different from each other, and two or more of $X^4$, $X^5$, and $X^6$ may bond to each other to form a ring.

$R^{41}$, $R^{42}$, $R^{43}$, $R^{44}$, $R^{45}$, $R^{46}$, $R^{47}$, and $R^{48}$ each represent a hydrogen atom or a hydrocarbyl group.]

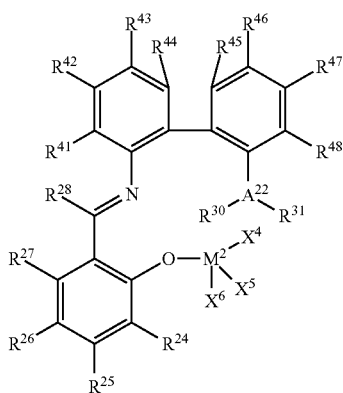

(2-b)

[$M^2$, $A^{21}$, $R^{24}$, $R^{25}$, $R^{26}$, $R^{27}$, $R^{28}$, $R^{30}$, $R^{31}$, $X^4$, $X^5$, and $X^6$ in the general formula (2-b) are respectively same as the above $M^2$, $A^{21}$, $R^{24}$, $R^{25}$, $R^{26}$, $R^{27}$, $R^{28}$, $R^{30}$, $R^{31}$, $X^4$, $X^5$, and $X^6$. Two selected from $R^{24}$, $R^{25}$, $R^{26}$, $R^{27}$, and $R^{28}$ may be bonded to each other at a site thereof formed by removing a hydrogen atom from the substituent group. $X^4$, $X^5$, and $X^6$ may be same as or different from each other, and two or more of $X^4$, $X^5$, and $X^6$ may bond to each other to form a ring.
$R^{41}$, $R^{42}$, $R^{43}$, $R^{44}$, $R^{45}$, $R^{46}$, $R^{47}$, and $R^{48}$ each represent a hydrogen atom or a hydrocarbyl group.]

A preferred atom as $M^2$ in the general formula (2-a) and the general formula (2-b) is same as the preferred atom as $M^2$ in the general formula (2-4) and the general formula (2-5).

Preferred atoms or groups as $R^{24}$, $R^{25}$, $R^{26}$, $R^{27}$, $R^{28}$, and $X^4$ in the general formula (2-a) and the general formula (2-b) are same as the preferred atoms or groups as $R^{24}$, $R^{25}$, $R^{26}$, $R^{27}$, $R^{28}$, $X^4$, $X^5$, and $X^6$ in the general formula (2-4) and the general formula (2-5).

Preferred groups as $R^{29}$, $R^{30}$, and $R^{31}$ in the general formula (2-a) and the general formula (2-b) are same as the preferred groups as $R^{29}$, $R^{30}$, and $R^{31}$ in the general formula (2-4) and the general formula (2-5).

$R^{41}$, $R^{42}$, $R^{43}$, $R^{44}$, $R^{45}$, $R^{46}$, $R^{47}$, and $R^{48}$ in the general formula (2-a) and the general formula (2-b) each represent a hydrogen atom or a hydrocarbyl group. Preferably, the hydrocarbyl group is an alkyl group. The number of carbon atom(s) of the hydrocarbyl group is, preferably, 1 to 10 and is, more preferably, 1 to 5.

The production method of the olefin oligomerization reaction catalyst of the present invention can be a method of bringing the modified solid polyalkylaluminoxane and a transition metal complex into contact with each other and can be, for example, a method according to which a solid polyalkylaluminoxane, and a halogenated alcohol including 1 to 20 carbon atoms or a halogenated phenol including 6 to 20 carbon atoms are caused to react with each other in a solvent to acquire the modified solid polyalkylaluminoxane, and a transition metal complex is thereafter brought into contact therewith. Preferably, the reaction of the solid polyalkylaluminoxane, and the halogenated alcohol including 1 to 20 carbon atoms or the halogenated phenol including 6 to 20 carbon atoms is caused to take place before the contact with the transition metal complex. A part of all of these operations may be executed in a reactor for the olefin oligomerization reaction. The olefin oligomerization reaction catalyst may be used as slurry as it is after the contact, or may be used as a solid substance acquired by removing the solvent from the slurry by filtering, decantation, or reduced-pressure distillation of the solvent, etc.

Preferably, the modified solid polyalkylaluminoxane and the transition metal complex are brought into contact with each other in a solvent. The solvent can be, for example, an aliphatic hydrocarbon such has butane, pentane, hexane, heptane, or octane, and an aromatic hydrocarbon such as benzene or toluene. Each of these solvents may be used alone, or two or more thereof may be used as a mixture. The use amount thereof is, preferably, 1 part by weight to 200 parts by weight and is, more preferably, 3 parts by weight to 50 parts by weight relative to one part by weight of the modified solid polyalkylaluminoxane.

The temperature for bringing the modified solid polyalkylaluminoxane and the transition metal complex into contact with each other is usually equal to or higher than −30° C. and equal to or lower than the boiling point of the solvent, is, preferably, −10° C. to 120° C., and is, more preferably, 0° C. to 50° C.

When the slurry after the contact is used as the olefin oligomerization reaction catalyst, the mol concentration of the aluminum atoms contained in the modified solid polyalkylaluminoxane in the olefin oligomerization reaction catalyst is usually 0.01 mmol/L to 500 mmol/L and is, preferably, 0.02 mmol/L to 100 mmol/L. The mol concentration of the transition metal complex contained in the olefin oligomerization reaction catalyst is usually 0.0001 mmol/L to 5 mmol/L and is, preferably, 0.0002 mmol/L to 1 mmol/L.

The mol ratio of the aluminum atoms contained in the modified solid polyalkylaluminoxane to the transition metal complex is usually 1 to 10.000, is, preferably, 10 to 1,000, and is, more preferably, 50 to 500.

The olefin oligomerization reaction catalyst may be used in combination with one or more type(s) of aluminum compound (A) represented by a general formula (A).

$(E^1)_a Al(G)_{3-a}$      General Formula (A).

(In the general formula (A), $E^1$ represents a hydrocarbyl group having 1 to 8 carbon atoms, G represents a hydrogen atom or a halogen atom, and "a" is a number 1 to 3. When "a" is equal to or greater than 2, the plural $E^1$s may be same as or different from each other.

The hydrocarbyl group having 1 to 8 carbon atoms as $E^1$ can be, for example, an alkyl group having 1 to 8 carbon atoms and can be, for example, a methyl group, an ethyl group, an n-propyl group, an isopropyl group, an n-butyl group, an isobutyl group, an n-pentyl group, and a neopentyl group.

An organic aluminum compound (A) can be, for example, a trialkyl aluminum, a dialkyl aluminum chloride, an alkyl aluminum dichloride, and a dialkyl aluminum hydride. The trialkyl aluminum can be, for example, trimethyl aluminum, triethyl aluminum, tripropyl aluminum, triisobutyl aluminum, trihexyl aluminum, and trioctyl aluminum. The dialkyl aluminum chloride can be, for example, dimethyl aluminum chloride, diethyl aluminum chloride, dipropyl aluminum chloride, diisobutyl aluminum chloride, dihexyl aluminum chloride, and dioctyl aluminum chloride. The alkyl aluminum dichloride can be, for example, methyl aluminum dichloride, ethyl aluminum dichloride, propyl aluminum dichloride, isobutyl aluminum dichloride, hexyl aluminum dichloride, and octyl aluminum dichloride. The dialkyl aluminum hydride can be, for example, dimethyl aluminum hydride, diethyl aluminum hydride, dipropyl aluminum hydride, diisobutyl aluminum hydride, dihexyl aluminum dydride, and dioctyl aluminum hydride. Preferably, trimethyl aluminum, triisobutyl aluminum, or trioctyl aluminum is used.

The mol ratio of the aluminum compound (A) to the transition metal complex is usually 1 to 100,000 and is, preferably, 100 to 50,000. The mol concentration of the organic aluminum compound (A) is usually 0.01 mmol/L to 500 mmol/L and is, preferably, 0.1 mmol/L to 100 mmol/L.

The olefin oligomerization reaction catalyst of the present invention is usable in an olefin oligomerization reaction and can, for example, oligomerize an olefin to produce α-olefins. For example, 1-butene, 1-hexene, and 1-octene can be produced from ethylene.

The olefin oligomerization reaction catalyst of the present invention is, preferably, used in a reaction to produce 1-hexene or 1-octene from ethylene and is, more preferably, used in a reaction to produce 1-hexene from ethylene.

The olefin oligomerization reaction may be conducted in a solvent such as an aliphatic hydrocarbon such as butane, pentane, hexane, heptane, or octane, or an aromatic hydrocarbon such as benzene or toluene. This reaction may be executed using the slurry or may be executed using an olefin in a gas form.

The olefin oligomerization reaction can be conducted in any one method of a batch-wise method, a semicontinuous method, and a continuous method.

When an olefin taking a gas form at ordinary pressure is used as the raw material olefin, the pressure of this olefin is usually equal to or higher than ordinary pressure and equal to or lower than 10 MPa and is, preferably, 0.5 MPa to 5 MPa.

The temperature of the olefin oligomerization reaction is usually −50° C. to 220° C., and is, preferably, 0° C. to 170° C., and is, more preferably, 30° C. to 100° C.

Though the reaction time of the olefin oligomerization reaction is generally determined properly depending on the used reaction apparatus, preferably, the reaction time is 1 minute to 20 hours.

EXAMPLES

The present invention will be described with reference to Examples and Comparative Examples.
<Production of 1-Hexene>
(1) Yield of 1-Hexene and Decenes
An analysis was conducted by gas chromatography using a usual internal standard method employing the following conditions.
Measuring Apparatus: GC-2010 (Shimadzu Corporation)
Column: DB-1, 60 m, Membrane thickness 0.25 μm, Internal diameter 0.25 mm
Temperature Increase Pattern: Maintaining 50° C. for 10 min, subsequently increasing the temperature to 200° C. at 5° C./min, and subsequently maintaining 200° C. for 20 min.
Temperature in Vaporizing Chamber: 230° C.
Temperature of Detector: 230° C.
Split Ratio: 39
Carrier Gas: Helium
Internal Standard: n-nonane
(2) Yield of Polymer
The reaction solution was put in a mixture solvent including ethanol and methanol, and a precipitated composition was collected by filtering. The composition was dried at a reduced pressure at 80° C. and the weight of the composition was measured to acquire the yield.

(3) Measurement Method of Median Diameter and Particle Size Distribution of Each of Silica/Polymethylaluminoxane, Solid Polymethylaluminoxane, and Modified Solid Polymethylaluminoxane The median diameter and the particle size distribution of each of the solid polymethylaluminoxane and the modified solid polymethylaluminoxane were determined using the following measuring apparatus and using a laser diffraction scattering method in the following dried measurement solvent.
Measuring Apparatus: SALD-2200J
Measurement Solvent: n-hexane
The Span value was used as the index of the particle size distribution.

$$\text{Span value} = (D90 - D10)/D50$$

(D10, D50, and D90 respectively represent the values of the particle diameter when the values of the cumulative distribution function of the particle side distribution measured using the above method are 10%, 50%, and 90%.)
(4) Aluminum Content in Solid Polymethylaluminoxane and Modified Solid Polymethylaluminoxane The aluminum content in the solid polymethylaluminoxane and the modified solid polymethylaluminoxane was determined in the following way. The solid polymethylaluminoxane or the modified solid polymethylaluminoxane was first added into pure water under a nitrogen atmosphere, this was taken out in the air to be heated, and water was entirely evaporated. After adding sodium carbonate to the precipitated solid, which was then heated to melt, and the aluminum content was determined by the ICP-AES method, using Vista-PRO made by Varian Inc.
(5) Determination for m/(m+n) in General Formula (1)

The value of m/(m+n) was determined in the following way. In the preparation of the modified solid polymethylaluminoxane, when a halogenated alcohol or a halogenated phenol is added to the solid polymethylaluminoxane as a starting material, an equimolar amount of methane with the halogenated alcohol or halogenated phenol which had reacted will generate. In consideration of this, when the aluminum content of the solid polymethylaluminoxane is X wt %, the aluminum content of the modified solid polymethylaluminoxane is Y wt % and the molar weight of a halogenated alcohol or halogenated phenol is M, Y can be expressed in the following way in terms of X. M, and m/(m+n).

$$Y = \frac{X/100}{(M-16) \times \frac{X}{100 \times 27} \times m/(m+n) + 1} \times 100 \; (wt\%)$$

Thus, the value of m/(m+n) can be determined by the following formula.

$$m/(m+n) = \frac{2700(X-Y)}{(M-16)XY}$$

(6) Activity of Olefin Oligomerization Reaction Catalyst

As the indexes of the catalyst activity, values acquired by dividing the weight of 1-hexene obtained by the reaction by the substance quantity of the used complex (t/mol complex), and values acquired by dividing the weight of the 1-hexene obtained by the reaction by the weight of the used cocatalyst (silica/polymethylaluminoxane, the solid polymethylaluminoxane, or the modified solid polymethylaluminoxane) (g/g co-catalyst).

(7) Synthesis of Known Transition Metal Complex

The titanium complexes of the following formulas (8) and (9) (hereinafter, respectively referred to as "complex 1" and "complex 2") were synthesized according to a known approach (Japanese Laid-Open Patent Publication No. 2011-98954) and the titanium complex of the following formula (10) (hereinafter, referred to as "complex 3") was synthesized according to a known approach (WO 2009-005003).

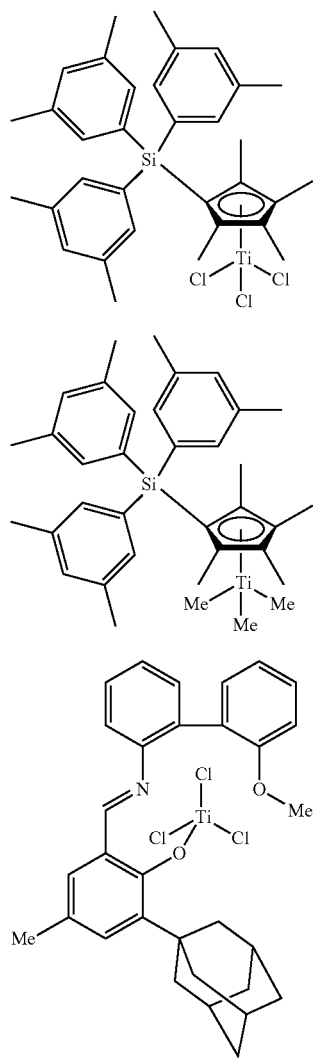

(8)

(9)

(10)

(8) Synthesis of Known Ligand

N,N'-bis(diphenylphosphino)isopropylamine was synthesized in accordance with the known method (A. Bollmann, et al. J. Am. Chem. Soc. 2004, 126, 14712.).

Reference Example 1

1 g of silica gel (produced by GRACE-Davison, Sylopol 948; the median diameter=55 μm) was dried for 5 hours at 300° C. under a nitrogen atmosphere and was weighed in a 200 mL flask. 15 mL of dehydrated toluene was added to the silica gel. After the substances in the flask was cooled at 0° C. in an ice bath, 5.0 mL of a toluene solution (17.5 mmol) of polymethylaluminoxane whose concentration of aluminum contained in the toluene solution was 3.5 mmol/mL (produced by Tosoh Finechem Corporation) was slowly added to the substances in the flask taking 30 min, using a dripping funnel and stirring the substances. After the dripping, the temperature was increased to 95° C. to be stirred for 4 hours. After the reaction, the temperature was decreased to the room temperature and the supernatant solution was removed by decantation. 15 mL of toluene was further added to the residue to be stirred and the mixture was left untouched. The supernatant solution was again removed by decantation. This washing operation was repeated three times and, finally, the residue was dried at a reduced pressure at 100° C. for 1 hour to obtain the target silica/polymethylaluminoxane. The yield was 1.2 g and, as the result of an elemental analysis (wt %), the residue contained Si:24% and Al:19%.

Reference Example 2

95.3 g of silica gel (produced by GRACE-Davison, Sylopol 948; the median diameter=55 μm) was dried for 5 hours at 300° C. under a nitrogen atmosphere and was put in a flask whose inside was substituted by argon. 550 ml of toluene was put in the flask and the flask was put in an ice bath. In the ice bath, a toluene solution of polymethylaluminoxane whose concentration of aluminum contained in the toluene solution was 3.4 mmol/mL (produced by Tosoh Finechem Corporation) was added to the mixture in the flask over 1 hour. After stirring the mixture for 1 hour in the ice bath, the temperature was increased to 50° C., and the mixture was stirred for 4 hours. The supernatant was thereafter removed, and the solid was washed twice with 500 ml of toluene and once with 500 ml of hexene. The residue was dried at a reduced pressure to obtain 140.1 g of silica/polymethylaluminoxane.

Reference Example 3

0.81 g of a solid polymethylaluminoxane (produced by Tosoh Finechem Corporation, aluminum atoms=39.9 wt %, median diameter=17 μm, Span value=1.4) and 20 mL of toluene were added into a 100 mL two-necked flask that was heated and dried at 110° C. for 30 min or longer, to prepare a slurry. A solution of 0.433 g of pentafluorophenol in 1.5 mL of toluene was added to the slurry stirred at room temperature, and the mixture was further stirred for 3 hours. After the liquid was removed by filtration using a glass filter, the resulting solid was washed twice with 20 mL of toluene and once with 20 mL of hexane. The solid was dried at a reduced pressure for 1 hour to obtain 1.11 g of the modified solid polymethylaluminoxane as white powder. (Median diameter=7 μm, Span value=1.5). As a result of the elemental analysis, the aluminum content was 26 wt %, and the value of m/(m+n) in the general formula (1) was 0.21.

Reference Examples 4-8

Each modified solid polymethyl aluminoxane was prepared similarly, in which the used amounts of the solid polymethylaluminoxane and pentafluorophenol in Reference Example 3 were changed. The used amounts of materials and the results are shown in Table 1.

TABLE 1

| | Solid Polymethyl aluminoxane (g) | Pentafluorophenol (g) | Yield (g) | Median diameter (μm) | Span value | Aluminum content (wt %) | m/(m + n) |
|---|---|---|---|---|---|---|---|
| R. Ex. 3 | 0.81 | 0.433 | 1.11 | 7 | 1.5 | 26 | 0.21 |
| R. Ex. 4 | 0.79 | 0.21 | 0.90 | — | — | — | — |
| R. Ex. 5 | 0.79 | 0.64 | 1.24 | — | — | — | — |
| R. Ex. 6 | 0.50 | 0.54 | 0.89 | — | — | 20 | 0.39 |
| R. Ex. 7 | 1.00 | 1.34 | 2.17 | — | — | 18 | 0.48 |
| R. Ex. 8 | 0.50 | 0.81 | 1.15 | — | — | 16 | 0.59 |

Reference Example 9

A solid polymethylaluminoxane was prepared in accordance with the known method (JP 2000-95810 A). A modified solid polymethyl aluminoxane 0.85 g was prepared in the same method as that of Reference Example 3, in which 0.45 g of the solid polymethylaluminoxane and 0.61 g of pentafluorophenol were used. (Median diameter=64 μm, Span value=2.0)

Reference Example 10

95 mg of complex 1, 8 mL of toluene, and 112 μL of triethylamine were added to a 20 mL Schlenk tube, whose inside had been substituted with nitrogen. Next, a solution of 46 mg of phenol in 2 mL of toluene was added there, and the resultant mixture was stirred at room temperature for 16 hours. The precipitate formed was removed under a nitrogen atmosphere by filtration, and the solvent and the excess triethylamine were distilled off at a reduced pressure. The product was extracted from the obtained solid with 3 mL of hexane, and after condensed to 1 mL at a reduced pressure, followed by one-night standing at −20° C., 97 mg of the titanium complex (henceforth "the complex 4") represented by the formula 11 was obtained as crystals.

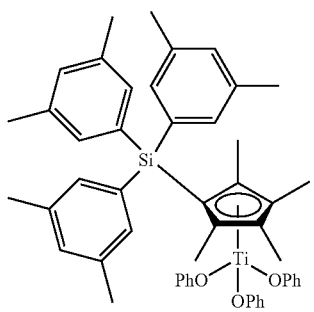

(11)

Example 1

1600 ml of heptane was added to a 5 L autoclave equipped with a stirrer whose inside was dried at a reduced pressure and was thereafter substituted by argon. The temperature in the system was increased to 40° C., and ethylene was introduced so that the partial pressure thereof became 3.0 MPa before stabilizing the temperature and the pressure in the system. 1.0 mL of a hexane solution of triisobutylaluminum whose concentration of triisobutylaluminum was 1.0 mmol/mL (produced by Tosoh Finechem Corporation) was added to the system. Then a slurry prepared by bringing 2 ml of heptane, 34 mg of the modified solid polymethylaluminoxane obtained in Reference Example 3, and 0.2 ml of a toluene solution of the complex 2 (5 μmol/ml) into contact with each other at room temperature for 1 minute was added. The reaction was continued at 40° C. for 5 hours with an ethylene gas continuously supplied thereto to maintain the total pressure to be constant. Ethylene was thereafter purged, and the content of the autoclave was demineralized using ethanol-hydrochloric acid and was filtered. 222 g of 1-hexene (222 t/mol complex, 6530 g/g co-catalyst), 12.5 g of decenes, and 4.2 g of a polymer were obtained. No adhesion of any formless polymer to the stirrer blades and so on was observed.

Example 2

1600 ml of heptane was added to a 5 L autoclave equipped with a stirrer whose inside was dried at a reduced pressure and was thereafter substituted by argon. The temperature in the system was increased to 40° C., and ethylene was introduced so that the partial pressure thereof became 2.0 MPa before stabilizing the temperature and the pressure in the system. 1.0 mL of a hexane solution of triisobutylaluminum whose concentration of triisobutylaluminum was 1.0 mmol/mL (produced by Tosoh Finechem Corporation) was added to the system. Then a slurry prepared by bringing 2 ml of heptane, 63 mg of the modified solid polymethylaluminoxane obtained in Reference Example 3, and 0.4 ml of a toluene solution of the complex 2 (5 μmol/ml) into contact at room temperature for 1 minute with each other was added. The reaction was continued at 40° C. for 5 hours with an ethylene gas continuously supplied thereto to maintain the total pressure to be constant. Ethylene was thereafter purged, and the content of the autoclave was demineralized using ethanol-hydrochloric acid and was filtered. 294 g of 1-hexene (147 t/mol complex, 4670 g/g co-catalyst), 34.7 g of decenes, and 4.7 g of a polymer were obtained. No adhesion of any formless polymer to the stirrer blades and so on was observed.

Comparative Example 1

1200 ml of heptane was added to a 5 L autoclave equipped with a stirrer whose inside was dried at a reduced pressure and was thereafter substituted by argon. 1.8 mL of a toluene solution of polymethylaluminoxane whose concentration of aluminum contained in the toluene solution was 3.4 mmol/mL (produced by Tosoh Finechem Corporation) was added to the system. The temperature in the system was increased to 40° C., and ethylene was introduced so that the partial pressure thereof became 2.0 MPa before stabilizing the temperature and the pressure in the system. Then a mixture of 0.29 mL of a toluene solution of polymethylaluminoxane whose concentration of aluminum contained in the toluene solution was 3.4 mmol/mL (produced by Tosoh Finechem Corporation) and 0.4 ml of a toluene solution of the complex 2 (5 μmol/ml) was added. The reaction was continued at 40° C. for 90 minutes with an ethylene gas continuously supplied thereto to maintain the total pressure to be constant. Ethylene was thereafter purged, and the content of the autoclave was demineralized using ethanol-hydrochloric acid and was filtered. 184 g of 1-hexene (92 t/mol complex), 23 g of decenes, and 1.0 g of a polymer were obtained. Adhesion of a formless polymer to the stirrer blades and so on was observed.

Comparative Example 2

800 ml of heptane was added to a 5 L autoclave equipped with a stirrer whose inside was dried at a reduced pressure and was thereafter substituted by argon. 1.5 mL of a hexane solution of triisobutylaluminum whose concentration of triisobutyl aluminum was 1.0 mmol/ml, (produced by Tosoh Finechem Corporation) was added to the system. The temperature in the system was increased to 40° C., and ethylene was introduced so that the partial pressure thereof to be 2.0 MPa before stabilizing the temperature and the pressure in the system. Then a mixture of 0.29 mL of a toluene solution of polymethylaluminoxane whose concentration of aluminum contained in the toluene solution was 3.4 mmol/mL (produced by Tosoh Finechem Corporation) and 0.4 ml of a toluene solution of the complex 2 (5 μmol/ml) was added. The reaction was continued at 40° C. for 60 minutes with an ethylene gas continuously supplied thereto to maintain the total pressure to be constant. The ethylene was thereafter purged, and the content of the autoclave was demineralized using ethanol-hydrochloric acid and was filtered. 18 g of 1-hexene (9 t/mol complex), 0.05 g of decenes, and 0.7 g of a polymer were obtained. Adhesion of a formless polymer to the stirrer blades and so on was observed.

Comparative Example 3

Under a nitrogen atmosphere, 5 mL of toluene was added in a flask. 0.2 μmol of the complex 1 and 194 mg of silica/polymethylaluminoxane obtained in Reference Example 1 were added in the flask and stirred for 5 minutes. Toluene as the solvent was distilled at a reduced pressure to obtain a solid substance.

90 ml of toluene and 2.2 mL, of a hexane solution of triisobutylaluminum whose concentration was 0.93 mmol/mL (produced by Tosoh Finechem Corporation) were added to a 0.4 L autoclave equipped with a stirrer whose inside was dried at a reduced pressure and was thereafter substituted by argon. The temperature in the system was increased to 40° C., and ethylene was thereafter introduced so that the partial pressure thereof became 2.0 MPa before stabilizing the temperature and the pressure in the system. 106 mg of the solid substance contained as above was added to this. The reaction was continued at 40° C. for 60 minutes with an ethylene gas continuously supplied thereto to maintain the total pressure to be constant. 2.0 mL of ethanol was added to the system to stop the reaction. Ethylene was thereafter purged, and the content of the autoclave was demineralized using ethanol-hydrochloric acid and was filtered. 7.6 g of 1-hexene (38 t/mol complex, 72 g/g co-catalyst), 0.5 g of a polymer were obtained. No adhesion of any formless polymer to the stirrer blades and so on was observed.

Comparative Example 4

1600 ml of heptane was added to a 5 L autoclave equipped with a stirrer whose inside was dried at a reduced pressure and was thereafter substituted by argon. 1.0 mL of a hexane solution of triisobutylaluminum whose concentration was 1.0 mmol/mL (produced by Tosoh Finechem Corporation) was added to the system. The temperature in the system was increased to 40° C., and ethylene was introduced so that the partial pressure thereof became 2.0 MPa before stabilizing the temperature and the pressure in the system. Then a mixture of 4.0 ml of heptane, 294 mg of a solid polymethylaluminoxane (produced by Tosoh Finechem Corporation, aluminum atoms=39.3 wt %), and 0.8 ml of a toluene solution of the complex 2 (5 μmol/ml) was added. The reaction was continued at 40° C. for 120 minutes with an ethylene gas continuously supplied thereto to maintain the total pressure to be constant. The ethylene was thereafter purged and the content of the autoclave was demineralized using ethanol-hydrochloric acid and was filtered. 231 g of 1-hexene (58 t/mol complex, 785 g/g co-catalyst), 18.3 g of decenes, and 3.5 g of a polymer were obtained. Adhesion of a formless polymer to the stirrer blades and so on was observed.

Comparative Example 5

1600 ml of heptane was added to a 5 L autoclave equipped with a stirrer whose inside was dried at a reduced pressure and was thereafter substitute by argon. 1.0 mL of a hexane solution of triisobutylaluminum whose concentration was 1.0 mmol/mL (produced by Tosoh Finechem Corporation) was added to the system. The temperature in the system was increased to 40° C., and ethylene was introduced so that the partial pressure thereof became 2.0 MPa before stabilizing the temperature and the pressure in the system. Then a mixture of 4.0 ml of heptane, 282 mg of a solid polymethylaluminoxane (produced by Tosoh Finechem Corporation, aluminum atoms=39.3 wt %), and 0.8 ml of a toluene solution of the complex 1 (5 μmol/m) was added. The reaction was continued at 40° C. for 120 minutes with an ethylene gas continuously supplied thereto to maintain the total pressure to be constant during the reaction. Ethylene was thereafter purged, and the content of the autoclave was demineralized using ethanol-hydrochloric acid and was filtered. 230 g of 1-hexene (57 t/mol complex, 815 g/g co-catalyst), 18.3 g of decenes, and 3.6 g of a polymer were obtained. No adhesion of any formless polymer to the stirrer blades and so on was observed.

Example 3

120 ml of heptane was added to a 0.4 L autoclave equipped with a stirrer whose inside was dried at a reduced pressure and was thereafter substitute by argon. The temperature in the system was increased to 40° C., and ethylene was introduced so that the partial pressure thereof became 2.0 MPa before stabilizing the temperature and the pressure in the system. 0.40 mL of a hexane solution whose trioctylaluminum concentration was 1.01 mmol/ml (produced by Tosoh Finechem Corporation) was added to the system. Then a slurry prepared by stirring a mixture of 3 ml of toluene, 33 mg of the modified solid polymethylaluminoxane obtained in Reference Example 3, and 1.0 ml of a toluene solution of the complex 3 (1 μmol/ml) at room temperature for an hour was added. The reaction was continued at 40° C. for 60 minutes with an ethylene gas continuously supplied thereto to maintain the total pressure to be constant during the reaction. Ethylene was thereafter purged, and the content of the autoclave was demineralized using ethanol-hydrochloric acid and was filtered. 24 g of 1-hexene (24 t/mol complex, 727 g/g co-catalyst) and 1.5 g of a polymer were obtained. No adhesion of any formless polymer to the stirrer blades and so on was observed.

Comparative Example 6

120 ml of heptane was added to a 0.4 L autoclave equipped with a stirrer whose inside was dried at a reduced pressure and was thereafter substitute by argon. The temperature in the system was increased to 40° C., and ethylene was introduced so that the partial pressure thereof became 2.0 MPa before stabilizing the temperature and the pressure in the system. 0.40 mL of a hexane solution whose trioctylaluminum concentration was 1.01 mmol/ml (produced by Tosoh Finechem Corporation) was added to the system. Then a slurry prepared by stirring 3 ml of toluene, 34 mg of the silica/polymethylaluminoxane obtained in Reference Example 2, and 1.0 ml of a toluene solution of the complex 3 (1 μmol/ml) at room temperature and for an hour was added. The reaction was continued at 40° C. for 60 minutes with an ethylene gas continuously supplied thereto to maintain the total pressure to be constant during the reaction. Ethylene was thereafter purged, and the content of the autoclave was demineralized using ethanol-hydrochloric acid and was filtered. 4.2 g of 1-hexene (4 t/mol complex, 123 g/g co-catalyst) and 0.2 g of a polymer were obtained. No adhesion of any formless polymer to the stirrer blades and so on was observed.

Comparative Example 7

120 ml of heptane was added to a 0.4 L autoclave equipped with a stirrer whose inside was dried at a reduced pressure and was thereafter substitute by argon. The temperature in the system was increased to 40° C., and ethylene was introduced so that the partial pressure thereof became 2.0 MPa before stabilizing the temperature and the pressure in the system. 0.40 mL of a hexane solution whose trioctylaluminum concentration was 1.01 mmol/ml (produced by Tosoh Finechem Corporation) was added to the system. Then a slurry prepared by stirring 3 ml of toluene, 14 mg of a solid polymethylaluminoxane (produced by Tosoh Finechem Corporation, aluminum atoms=39.3 wt %), and 1.0 ml of a toluene solution of the complex 3 (1 μmol/ml) at room temperature for an hour. The reaction was continued at 40° C. for 60 minutes with an ethylene gas continuously supplied thereto to maintain the total pressure to be constant during the reaction. Ethylene was thereafter purged, and the content of the autoclave was demineralized using ethanol-hydrochloric acid and was filtered. 17 g of 1-hexene (17 t/mol complex, 1214 g/g co-catalyst) and 1.5 g of a polymer were obtained. No adhesion of any formless polymer to the stirrer blades and so on was observed.

[Examples 4-16] and [Comparative Examples 8-11]

Experiments for trimerization reaction of ethylene were conducted by the same method as that in Examples 1 to 3 and Comparative Examples 1 to 7, in which the complex species, the alkylaluminum species, the co-catalyst species, reaction conditions, and so forth were changed as shown in Table 2. The results were summarized in Table 2.

TABLE 2

| | Reactor size | Solvent mL | complex | μmol | cocatalyst | mg | Trialkyl aluminum | mmol |
|---|---|---|---|---|---|---|---|---|
| Example 4 | 5 L | 2500 | complex 2 | 3 | Synthetic Example 4 | 48.2 | TiBA | 1.5 |
| Example 5 | 5 L | 2500 | complex 2 | 3 | Synthetic Example 3 | 66.1 | TiBA | 1.5 |
| Example 6 | 5 L | 2500 | complex 2 | 3 | Synthetic Example 5 | 75.4 | TiBA | 1.5 |
| Example 7 | 5 L | 2500 | complex 2 | 3 | Synthetic Example 6 | 80.4 | TiBA | 1.5 |
| Example 8 | 5 L | 2500 | complex 2 | 3 | Synthetic Example 6 | 84.1 | TMA | 5.0 |
| Example 9 | 5 L | 2500 | complex 2 | 3 | Synthetic Example 7 | 93.0 | TMA | 5.0 |
| Example 10 | 3 L | 1000 | complex 2 | 3 | Synthetic Example 7 | 23.2 | TMA | 1.0 |
| Example 11 | 3 L | 1000 | complex 4/TMA 1/10(mol ratio) | 3 | Synthetic Example 7 | 26.0 | TMA | 1.0 |
| Example 12 | 1 L | 400 | complex 2 | 1 | Synthetic Example 7 | 46.2 | TMA | 1.6 |
| Example 13 | 5 L | 2500 | complex 3 | 3 | Synthetic Example 2 | 64.0 | TNOA | 1.5 |
| Example 14 | 5 L | 2500 | complex 3 | 3 | Synthetic Example 6 | 86.2 | TNOA | 1.5 |
| Example 15 | 1 L | 400 | complex 3 | 3 | Synthetic Example 7 | 22.8 | TMA | 1.0 |
| Example 16 | 1 L | 400 | complex 4/TMA 1/20(mol ratio) | 1 | Synthetic Example 7 | 21.6 | TMA | 1.6 |
| Comparative Example 8 | 5 L | 2500 | complex 2 | 3 | solid polymethyl aluminoxane | 40.5 | TiBA | 1.5 |
| Comparative Example 9 | 1 L | 400 | complex 2 | 1 | Synthetic Example 8 | 51.2 | TMA | 1.6 |
| Comparative Example 10 | 5 L | 2500 | complex 3 | 3 | solid polymethyl aluminoxane | 57.6 | TNOA | 1.5 |
| Comparative Example 11 | 1 L | 400 | complex 4/TMA 1/20(mol ratio) | 1 | Synthetic Example 9 | 21.2 | TMA | 1.6 |

TABLE 2-continued

|  | Ethylene Pressure MPaG | Reaction temperature °C. | Reaction Time h | 1-Hexene activity t/mol-Ti | g/g-cocat. | Byproduct decenes g | Byproduct polymer g | Fouling |
|---|---|---|---|---|---|---|---|---|
| Example 4 | 3.0 | 40 | 3 | 49.5 | 3081 | 6.3 | 5.4 | Good |
| Example 5 | 3.0 | 40 | 3 | 56.6 | 2569 | 10.5 | 6.3 | Good |
| Example 6 | 3.0 | 40 | 3 | 67.1 | 2670 | 12.6 | 6.0 | Good |
| Example 7 | 3.0 | 40 | 3 | 82.9 | 3093 | 17.4 | 5.7 | Good |
| Example 8 | 3.0 | 40 | 3 | 83.3 | 2971 | 9.3 | 2.4 | Good |
| Example 9 | 3.0 | 40 | 3 | 82.3 | 2655 | 9.3 | 1.8 | Good |
| Example 10 | 4.5 | 40 | 3 | 83.1 | 10746 | 9.9 | 3.3 | Good |
| Example 11 | 4.5 | 40 | 3 | 98.7 | 11386 | 11.7 | 3.9 | Good |
| Example 12 | 1.8 | 40 | 4 | 92.2 | 1996 | 18.0 | 0.7 | Good |
| Example 13 | 3.0 | 40 | 3 | 39.4 | 1847 | 17.1 | 4.8 | Good |
| Example 14 | 3.0 | 40 | 3 | 53.4 | 1858 | 21.3 | 6.3 | Good |
| Example 15 | 4.5 | 40 | 3 | 66.7 | 8776 | 35.7 | 10.5 | Good |
| Example 16 | 1.8 | 40 | 4 | 57.6 | 2667 | 6.2 | 0.6 | Good |
| Comparative Example 8 | 3.0 | 40 | 3 | 33.3 | 2467 | 2.4 | 3.9 | Good |
| Comparative Example 9 | 1.8 | 40 | 4 | 82.0 | 1602 | 14.6 | 0.7 | Good |
| Comparative Example 10 | 3.0 | 40 | 3 | 34.2 | 1781 | 14.4 | 3.0 | Good |
| Comparative Example 11 | 1.8 | 40 | 4 | 38.8 | 1830 | 2.8 | 1.3 | Poor |

TMA: Trimethylaluminum,
TiBA: Triisobutylaluminum,
TNOA: Tri(n-octyl)aluminum
Fouling Good: Polymer fouling was not observed after trimerization reaction.
Poor: Polymer fouling was observed after trimerization reaction.

Example 17

120 ml of heptane was added to a 0.4 L autoclave equipped with a stirrer whose inside was dried at a reduced pressure and was thereafter substitute by argon. The temperature in the system was increased to 45° C., and ethylene was introduced so that the partial pressure thereof became 3.0 MPa before stabilize the temperature and the pressure in the system. Next, 0.24 mL of a trimethylaluminum toluene solution (2.07 mmol/mL, produced by Tosoh Finechem Corporation) was added to the system. Then, a slurry composed of 2 mL of toluene and 152 mg of modified solid polymethylaluminoxane obtained by Reference Example 7 was charged. Furthermore, a mixture of a toluene solution (20 µmol/mL, 0.25 mL) of tris(2,4-pentanedionato)chromium (produced by Tokyo Kasei Kogyo Co., Ltd.) and a toluene solution (27 µmol/mL, 0.25 mL) of N,N'-bis(diphenylphosphino)isopropylamine which were mixed and allowed to stand for 5 minutes was charged, and the reaction was started. The reaction was continued at 45° C. for 120 minutes with an ethylene gas continuously supplied thereto to maintain the total pressure to be constant. Then, 1 mL of ethanol was added to stop the reaction, ethylene was purged, and the content in the autoclave was filtered.

The result is shown in Table 3.

Comparative Example 12

An experiment was conducted using the same method as that of Example 17 except that 69 mg of solid polymethylaluminoxane was used instead of modified solid polymethylaluminoxane. The result is shown in Table 3.

Comparative Example 13

An experiment was conducted using the same method as that of Example 17 except that 2.29 mL of a toluene solution of polymethylaluminoxane (produced by Tosoh Finechem Corporation) having an aluminium concentration of 0.44 mmol/mL was used instead of modified solid polymethylaluminoxane. The result is shown in Table 3.

TABLE 3

|  | 1-Hexene | | | 1-Octene | | | Polymer | |
|---|---|---|---|---|---|---|---|---|
|  | g | t/mol-Cr | g/g-cocat | g | t/mol-Cr | g/g-cocat | g | Fouling |
| Example 17 | 8.0 | 1.6 | 53 | 31.7 | 6.3 | 209 | 2.5 | Good |
| Comparative Example 12 | 1.3 | 0.3 | 19 | 5.8 | 1.2 | 84 | 0.5 | Good |
| Comparative Example 13 | 2.5 | 0.5 | — | 14.7 | 2.9 | — | 0.2 | Poor |

Good: No polymer fouling (adhesion of polymer to the reactor or stirrer blades) was observed.
Poor: Polymer fouling (adhesion of polymer to the reactor or stirrer blades) was observed.

The invention claimed is:

1. A modified solid polyalkylaluminoxane for olefin oligomerization reactions, the modified polyalkylaluminoxane having a median diameter of 0.1 µm to 50 µm and comprising structural units represented by the following general formula (a), and structural units represented by the following general formula (b),

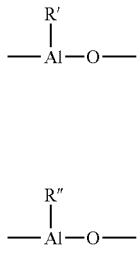

(a)

(b)

in which R' in the general formula (a) represents an alkyl group having 1 to 20 carbon atoms; and R" in the general formula (b) represents a halogenated alkoxy group having 1 to 20 carbon atoms or a halogenated aryloxy group having 6 to 20 carbon atoms.

2. The modified solid polyalkylaluminoxane of claim 1, wherein

R" in the general formula (b) is a halogenated aryloxy group having 6 to 20 carbon atoms.

3. The modified solid polyalkylaluminoxane of claim 2, wherein the halogenated aryloxy group having 6 to 20 carbon atoms is a pentafluorophenoxy group.

4. The modified solid polyalkylaluminoxane of claim 1, wherein the ratio (m/(m+n)) of the number (m) of the structural units represented by the general formula (b) to the total of the number (n) of the structural units represented by the general formula (a) and the number (m) of the structural units represented by the general formula (b) is 0.05 to 0.5.

5. An olefin oligomerization reaction catalyst comprising the modified solid polyalkylaluminoxane of claim 1 and at least one complex selected from the following group of transition metal complexes, wherein the group of transition metal complexes is a group consisting of transition metal complexes represented by the following general formula (2-1), transition metal complexes represented by the following general formula (2-2), transition metal complexes represented by the following general formula (2-3), transition metal complexes represented by the following general formula (2-4), and transition metal complexes represented by the following general formula (2-5),

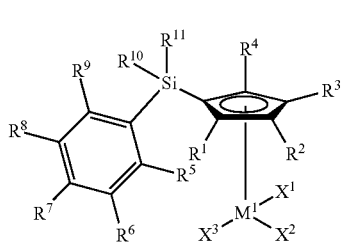

(2-1)

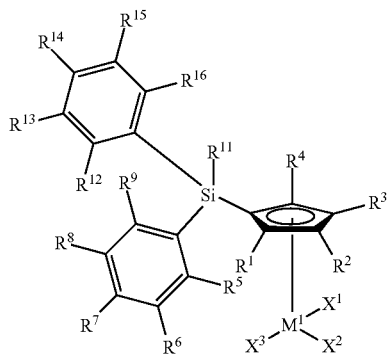

(2-2)

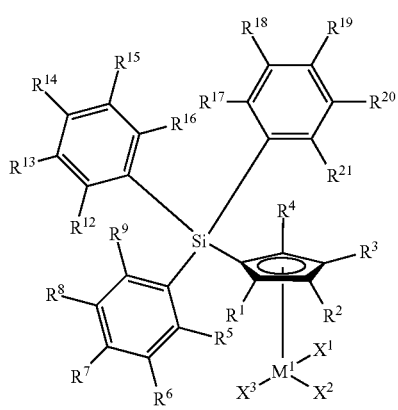

(2-3)

in which $M^1$ in each of the general formula (2-1), the general formula (2-2), and the general formula (2-3) represents a transition metal atom of Group 4 of the periodic table of the elements;

$X^1$, $X^2$, $X^3$, $R^1$, $R^2$, $R^3$, $R^4$, $R^5$, $R^6$, $R^7$, $R^8$, and $R^9$ in each of the general formula (2-1), the general formula (2-2), and the general formula (2-3), $R^{12}$, $R^{13}$, $R^{14}$, $R^{15}$, and $R^{16}$ in each of the general formula (2-2) and the general formula (2-3), and $R^{17}$, $R^{18}$, $R^{19}$, $R^{20}$, and $R^{21}$ in the general formula (2-3) each independently represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group;

when two selected from $R^1$, $R^2$, $R^3$, and $R^4$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^1$, $R^2$, $R^3$, and $R^4$ are optionally bonded to each other at a site thereof formed by removing a hydrogen atom from the substituent group;

when two selected from $R^5$, $R^6$, $R^7$, $R^8$, and $R^9$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^5$, $R^6$, $R^7$, $R^8$, and $R^9$ are optionally bonded to each other at a site thereof formed by removing a hydrogen atom from the substituent group;

when two selected from $R^{12}$, $R^{13}$, $R^{14}$, $R^{15}$, and $R^{16}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{12}$, $R^{13}$, $R^{14}$, $R^{15}$, and $R^{16}$ are optionally bonded to each other at a site thereof formed by removing a hydrogen atom from the substituent group;

when two selected from $R^{17}$, $R^{18}$, $R^{19}$, $R^{20}$, and $R^{21}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{17}$, $R^{18}$, $R^{19}$, $R^{20}$, and $R^{21}$ are optionally bonded to each other at a site thereof formed by removing a hydrogen atom from the substituent group;

$R^{10}$ in the general formula (2-1) and $R^{11}$ in the general formula (2-1) and the general formula (2-2) each independently represent a hydrocarbyloxy group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group; and $R^{10}$ and $R^{11}$ may be bonded to each other at a site thereof formed by removing a hydrogen atom from the substituent group,

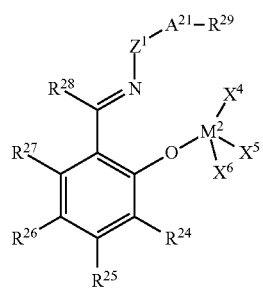

(2-4)

in which
M² in the general formula (2-4) represents a transition metal atom of Group 4 of the periodic table of the elements;
$A^{21}$ represents an oxygen atom, a nitrogen atom, a phosphorus atom, or a sulfur atom $Z^1$ represents a group linking $A^{21}$ and N to each other, and the smallest number of the bonds linking $A^{21}$ and N to each other is 4 to 6, and the bond linking $A^{21}$ and $Z^1$ to each other may be a double bond;
$R^{24}$, $R^{25}$, $R^{26}$, $R^{27}$, $R^{28}$, $X^4$, $X^5$, and $X^6$ each independently represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group;
when two selected from $R^{24}$, $R^{25}$, $R^{26}$, $R^{27}$, and $R^{28}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{24}$, $R^{25}$, $R^{26}$, $R^{27}$, and $R^{28}$ are optionally bonded to each other at a site thereof formed by removing a hydrogen atom from the substituent group;

$R^{29}$ represents a hydrogen atom, a halogen atom, a hydrocarbyl group having 1 to 20 carbon atoms, a substituted hydrocarbyl group having 1 to 20 carbon atoms, a hydrocarbylidene group having 1 to 20 carbon atoms, or a substituted hydrocarbylidene group having 1 to 20 carbon atoms, the bond linking $R^{29}$ and $A^{21}$ to each other may be a double bond, and $R^{29}$ may be bonded to $Z^1$,

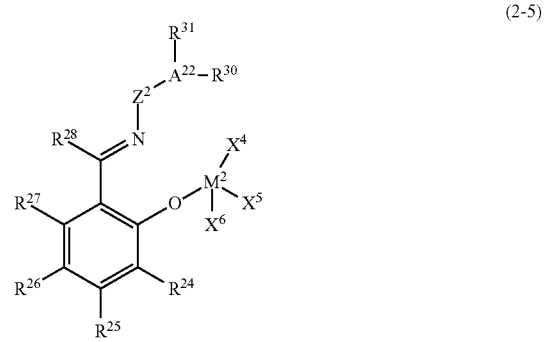

(2-5)

in which
M² in the general formula (2-5) represents a transition metal atom of Group 4 of the periodic table of the elements;
$A^{22}$ represents a nitrogen atom or a phosphorus atom, and $Z^2$ represents a group linking $A^{22}$ and N to each other and the smallest number of the bonds linking $A^{22}$ and N to each other is 4 to 6;
$R^{24}$, $R^{25}$, $R^{26}$, $R^{27}$, $R^{28}$, $X^4$, $X^5$, and $X^6$ each independently represent a hydrogen atom, a halogen atom, a hydrocarbyl group having 1 to 20 carbon atoms, a substituted hydrocarbyl group having 1 to 20 carbon atoms, a hydrocarbyloxy group having 1 to 20 carbon atoms, a substituted hydrocarbyloxy group having 1 to 20 carbon atoms, a substituted silyl group, or a disubstituted amino group;
when two selected from $R^{24}$, $R^{25}$, $R^{26}$, $R^{27}$, and $R^{28}$ each are a hydrocarbyl group having 1 to 20 carbon atoms, a substituted hydrocarbyl group having 1 to 20 carbon atoms, a hydrocarbyloxy group having 1 to 20 carbon atoms, or a substituted hydrocarbyloxy group having 1 to 20 carbon atoms, the two selected from $R^{24}$, $R^{25}$, $R^{26}$, $R^{27}$, and $R^{28}$ are optionally bonded to each other at a site thereof formed by removing a hydrogen atom from the substituent group; and
$R^{30}$ and $R^{31}$ each represent a hydrogen atom, a halogen atom, a hydrocarbyl group having 1 to 20 carbon atoms, or a substituted hydrocarbyl group having 1 to 20 carbon atoms, and $R^{30}$ or $R^{31}$ may be bonded to $Z^2$.

6. A method of producing 1-hexene, wherein 1-hexene is produced from ethylene in the presence of the olefin oligomerization reaction catalyst of claim 5.

* * * * *